United States Patent
Dochnahl et al.

(10) Patent No.: US 9,409,894 B2
(45) Date of Patent: Aug. 9, 2016

(54) CARBAMATES

(71) Applicant: BASF SE, Ludwigshafen (DE)

(72) Inventors: Maximilian Dochnahl, München (DE); Roland Götz, Neuluβheim (DE); Joachim Gebhardt, Wachenheim (DE); Uwe Josef Vogelbacher, Ludwigshafen (DE); Timo Frassetto, Mannheim (DE); Michael Rack, Eppelheim (DE); Volker Maywald, Ludwigshafen (DE); Bernd Wolf, Niederkirchen (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/421,321

(22) PCT Filed: Jul. 29, 2013

(86) PCT No.: PCT/EP2013/065872
§ 371 (c)(1),
(2) Date: Feb. 12, 2015

(87) PCT Pub. No.: WO2014/026845
PCT Pub. Date: Feb. 20, 2014

(65) Prior Publication Data
US 2015/0218139 A1 Aug. 6, 2015

Related U.S. Application Data

(60) Provisional application No. 61/684,159, filed on Aug. 17, 2012.

(30) Foreign Application Priority Data

Aug. 17, 2012 (EP) ..................... 12180823

(51) Int. Cl.
C07C 335/28 (2006.01)
C07C 275/60 (2006.01)
C07D 265/36 (2006.01)
C07D 413/04 (2006.01)

(52) U.S. Cl.
CPC ............ *C07D 413/04* (2013.01); *C07C 275/60* (2013.01); *C07C 335/28* (2013.01); *C07D 265/36* (2013.01)

(58) Field of Classification Search
CPC ... C07D 413/04; C07D 265/36; C07C 335/28
USPC .............................. 544/105, 221, 222; 564/23
See application file for complete search history.

(56) References Cited

U.S. PATENT DOCUMENTS

| | | | |
|---|---|---|---|
| 3,372,180 | A | 3/1968 | Ulrich |
| 3,392,184 | A | 7/1968 | Ulrich et al. |
| 4,418,073 | A | 11/1983 | Maurer et al. |
| 4,426,523 | A | 1/1984 | Dickore et al. |

FOREIGN PATENT DOCUMENTS

| | | |
|---|---|---|
| EP | 0 043 917 | 1/1982 |
| EP | 0 079 515 | 5/1983 |
| WO | WO 2010/145992 | 12/2010 |
| WO | WO 2011057935 | 5/2011 |
| WO | WO 2013092858 | 6/2013 |
| WO | WO 2014026928 | 2/2014 |

OTHER PUBLICATIONS

PubChem CID 53811040, Create Date: Dec. 4, 2011.*
PubChem Search Results, Sep. 5, 2015.*
International Search Report, PCT/EP2013/065872, filed Jul. 29, 2013, report completed Aug. 30, 2013.
International Preliminary Report on Patentability, PCT/EP2013/065872, filed Jul. 29, 2013, report completed Dec. 5, 2014.
European Search Report, EP12180823, search completed Nov. 21, 2012.
Andreani et al., "One-step synthesis and isolation of N-(tert.-butoxycarbonyl)-N'-methylthiourea on a large scale", Synthetic Communications, vol. 38, 2008, pp. 3834-3839.
Database Beilstein, Beilstein Institute for Organic Chemistry, Frankfurt, Germany, 1971, XP002712030.
Black et al., "Guanidino N-Substituted and N,N-Disubstituted Derivatives of the *K*-Opioid Antagonist GNTI", Journal of Medical Chemistry, vol. 46, 2003, pp. 5505-5511.
Biltz et al., "Substituted biurets and allophanic esters", Chemische Berichte, vol. 56, 1923, pp. 1914-1926.
Dains et al., "The action of ammonia and amines on the substituted areas and urethanes", Journal of the American Chemical Society, vol. 42, 1920, pp. 2303-2309.
Étienne et al., "No. 304—Diméthyl-3,5 trioxo-2,4,6 perhydro-oxadiazine-1,3,5 et dérivés (*)", Bulletin de la Societe Chimique de France, Jan. 1, 1974, pp. 1497-1505.
Linton et al., "A versatile one-pot synthesis of 1,3-substituted guanidines from carbamoyl isothiocyanates", The Journal of Organic Chemistry, vol. 65, No. 5, Mar. 10, 2003, pp. 1566-1568.
March, Advanced Organic Chemistry, $2^{nd}$ Ed., McGraw-Hill, 1977, p. 823, XP002687672.
Etienne et al., "Organic Chemistry—1,3-Diallyl 5 aryl Isocyanurates," C.R. Acad. Sc. Paris, Sep. 1, 1975, Series C-275, vol. 281.
Office Action dated Sep. 9, 2015 in U.S. Appl. No. 14/421,351.

* cited by examiner

*Primary Examiner* — Venkataraman Balasubramanian
(74) *Attorney, Agent, or Firm* — Brinks Gilson & Lione

(57) ABSTRACT

The present invention relates to carbamates of formula (I),

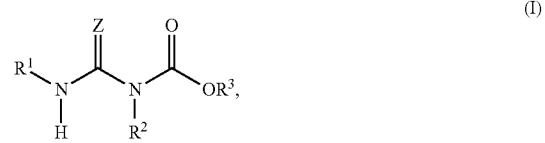

wherein the variables are defined according to the description,
as well as to a process for manufacturing carbamates of formula (I), and to the use of carbamates of formula (I) in manufacturing benzoxazinones of formula (VII).

8 Claims, No Drawings

CARBAMATES

This application is a National Stage application of International Application No. PCT/EP2013/065872, filed Jul. 29, 2013, which claims the benefit of U.S. Provisional Application No. 61/684,159, filed Aug. 17, 2012, the entire contents of which are hereby incorporated herein by reference. This application also claims priority under 35 U.S.C. §119 to EP Patent Application No. 12180823.2, filed Aug. 17, 2012, the entire contents of which is hereby incorporated herein by reference.

The invention relates to carbamates of formula (I), a process for manufacturing the same and their use for manufacturing benzoxazinones.

There is an ongoing need for plant protection compounds, for example herbicides, since weeds cause tremendous global economic losses by reducing crop yields and lowering crop quality. Accordingly there is also a need for efficient and improved manufacturing processes allowing the preparation of such plant protection compounds, for example herbicides.

Surprisingly it has been found that carbamates of formula (I) are potential intermediates for the preparation of active ingredients, for example for the preparation of the herbicidal active ingredients as described in WO 10/145992.

Accordingly, the present invention relates carbamates of formula (I),

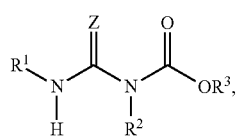

wherein
$R^1$ is H or $C_1$-$C_6$-alkyl;
$R^2$ is H or $C_1$-$C_6$-alkyl;
$R^3$ is $C_1$-$C_6$-alkyl, $C_1$-$C_6$-haloalkyl, $C_1$-$C_6$-cyanoalkyl, $C_1$-$C_6$-nitroalkyl, aryl, 5- or 6-membered heteroaryl or aryl-$C_1$-$C_6$-alkyl,
  wherein the aryl or heteroaryl rings are unsubstituted, partially or fully halogenated, or substituted by one to five substituents selected from the group consisting of CN, $NO_2$, $C_1$-$C_6$-alkyl, $C_1$-$C_6$-haloalkyl, OH, $C_1$-$C_6$-alkoxy, $C_1$-$C_6$-haloalkoxy, formyl, $C_1$-$C_6$-alkylcarbonyl, hydroxycarbonyl, and $C_1$-$C_6$-alkoxycarbonyl;
and
Z is O or S.

Further the present invention relates to a process for the preparation of carbamates of formula (I) by reacting (thio)urea compounds of formula (II) with chloroformic acid esters of formula (III) in the presence of a base.

In a further aspect of the present invention there is provided the use of carbamates of formula (I) in manufacturing benzoxazinones of formula (VII).

The organic moieties mentioned in the definition of the compounds and the substituents according to the invention, esp. of variables $R^1$ to $R^3$ are—like the term halogen—collective terms for individual enumerations of the individual group members. The term halogen denotes in each case fluorine, chlorine, bromine or iodine. All hydrocarbon chains, i.e. all alkyl, can be straight-chain or branched, the prefix $C_n$-$C_m$ denoting in each case the possible number of carbon atoms in the group.

Examples of such meanings are:
$C_1$-$C_4$-alkyl: for example $CH_3$, $C_2H_5$, n-propyl, $CH(CH_3)_2$ n-butyl, $CH(CH_3)$—$C_2H_5$, $CH_2$—$CH(CH_3)_2$ and $C(CH_3)_3$;
$C_1$-$C_6$-alkyl and also the $C_1$-$C_6$-alkyl moieties of $C_3$-$C_6$-cycloalkyl-$C_1$-$C_6$-alkyl, $C_1$-$C_6$-cyanoalkyl, $C_1$-$C_6$-nitroalkyl, aryl-$C_1$-$C_6$-alkyl, $C_1$-$C_6$-alkylcarbonyl: $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;
$C_1$-$C_4$-haloalkyl: a $C_1$-$C_4$-alkyl radical as mentioned above which is partially or fully substituted by fluorine, chlorine, bromine and/or iodine, for example, chloromethyl, dichloromethyl, trichloromethyl, fluoromethyl, difluoromethyl, trifluoromethyl, chlorofluoromethyl, dichlorofluoro-methyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, a $C_1$-$C_3$-haloalkyl radical as mentioned above, and also, for example, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl and 1-trifluoromethyl-1,2,2,2-tetrafluoroethyl;
$C_1$-$C_6$-haloalkyl: $C_1$-$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;
$C_3$-$C_6$-cycloalkyl and also the cycloalkyl moieties of $C_3$-$C_6$-cycloalkyl-$C_1$-$C_6$-alkyl: monocyclic saturated hydrocarbons having 3 to 6 ring members, such as cyclopropyl, cyclobutyl, cyclopentyl and cyclohexyl;
$C_3$-$C_6$-alkenyl: for example 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_2$-$C_6$-alkenyl: a $C_3$-$C_6$-alkenyl radical as mentioned above, and also ethenyl;

$C_3$-$C_6$-haloalkenyl: a $C_3$-$C_6$-alkenyl radical as mentioned above which is partially or fully substituted by fluorine, chlorine, bromine and/or iodine, for example 2-chloroprop-2-en-1-yl, 3-chloroprop-2-en-1-yl, 2,3-dichloroprop-2-en-1-yl, 3,3-dichloroprop-2-en-1-yl, 2,3,3-trichloro-2-en-1-yl, 2,3-dichlorobut-2-en-1-yl, 2-bromoprop-2-en-1-yl, 3-bromoprop-2-en-1-yl, 2,3-dibromoprop-2-en-1-yl, 3,3-dibromoprop-2-en-1-yl, 2,3,3-tribromo-2-en-1-yl or 2,3-dibromobut-2-en-1-yl;

$C_3$-$C_6$-alkynyl: for example 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

$C_2$-$C_6$-alkynyl: $C_3$-$C_6$-alkynyl as mentioned above and also ethynyl;

$C_3$-$C_6$-haloalkynyl: $C_3$-$C_6$-alkynyl as mentioned above which is partially or fully substituted by fluorine, chlorine, bromine and/or iodine, for example 1,1-difluoroprop-2-yn-1-yl, 3-chloroprop-2-yn-1-yl, 3-bromoprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_1$-$C_4$-alkoxy: for example methoxy, ethoxy, propoxy, 1-methylethoxy butoxy, 1-methylpropoxy, 2-methylpropoxy and 1,1-dimethylethoxy;

$C_1$-$C_6$-alkoxy and also the $C_1$-$C_6$-alkoxy moieties of $C_1$-$C_6$-alkoxy-$C_1$-$C_6$-alkyl, $C_1$-$C_6$-alkoxycarbonyl: $C_1$-$C_4$-alkoxy as mentioned above, and also, for example, pentoxy, 1-methylbutoxy, 2-methylbutoxy, 3-methoxybutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$-$C_4$-haloalkoxy: a $C_1$-$C_4$-alkoxy radical as mentioned above which is partially or fully substituted by fluorine, chlorine, bromine and/or iodine, i.e., for example, fluoromethoxy, difluoromethoxy, trifluoromethoxy, chlorodifluoromethoxy, bromodifluoromethoxy, 2-fluoroethoxy, 2-chloroethoxy, 2-bromomethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloro-ethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromo-ethoxy, 4-fluorobutoxy, 4-chlorobutoxy, 4-bromobutoxy and nonafluorobutoxy;

$C_1$-$C_6$-haloalkoxy: $C_1$-$C_4$-haloalkoxy as mentioned above, and also, for example, 5-fluoro-pentoxy, 5-chloropentoxy, 5-bromopentoxy, 5-iodopentoxy, undecafluoropentoxy, 6-fluoro-hexoxy, 6-chlorohexoxy, 6-bromohexoxy, 6-iodohexoxy and dodecafluorohexoxy;

aryl and also the aryl moieties of aryl-$C_1$-$C_6$-alkyl: a mono- to trinuclear aromatic carbocycle having 6 to 14 ring members, such as for example phenyl, naphthyl, anthracenyl and phenanthrenyl;

5- or 6-membered heteroaryl: an aromatic 5- or 6-membered monocyclic heterocycle which, in addition to carbon atoms comprises one to three nitrogen atoms, one or two nitrogen atoms and one sulfur atom, one nitrogen and one oxygen atom, one oxygen atom, or one sulfur atom as ring members, for example 5-membered aromatic rings such as like furyl (for example 2-furyl, 3-furyl), thienyl (for example 2-thienyl, 3-thienyl), pyrrolyl (for example pyrrol-2-yl, pyrrol-3-yl), pyrazolyl (for example pyrazol-3-yl, pyrazol-4-yl), isoxazolyl (for example isoxazol-3-yl, isoxazol-4-yl, isoxazol-5-yl), isothiazolyl (for example isothiazol-3-yl, isothiazol-4-yl, isothiazol-5-yl), imidazolyl (for example imidazole-2-yl, imidazole-4-yl), oxazolyl (for example oxazol-2-yl, oxazol-4-yl, oxazol-5-yl), thiazolyl (for example thiazol-2-yl, thiazol-4-yl, thiazol-5-yl), oxadiazolyl (for example 1,2,3-oxadiazol-4-yl, 1,2,3-oxadiazol-5-yl, 1,2,4-oxadiazol-3-yl, 1,2,4-oxadiazol-5-yl, 1,3,4-oxadiazol-2-yl), thiadiazolyl (for example 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl), triazolyl (for example 1,2,3-triazol-4-yl, 1,2,4-triazol-3-yl); and for example 6-membered aromatic rings such as pyridyl (for example pyridine-2-yl, pyridine-3-yl, pyridine-4-yl), pyrazinyl (for example pyridazin-3-yl, pyridazin-4-yl), pyrimidinyl (for example pyrimidin-2-yl, pyrimidin-4-yl, pyrimidin-5-yl), pyrazin-2-yl, triazinyl (for example 1,3,5-triazin-2-yl, 1,2,4-triazin-3-yl, 1,2,4-triazin-5-yl, 1,2,4-triazin-6-yl).

The preferred embodiments of the invention mentioned herein below have to be understood as being preferred either independently from each other or in combination with one another.

According to a preferred embodiment of the invention preference is also given to those carbamates of formula (I), wherein the variables, either independently of one another or in combination with one another, have the following meanings:

$R^1$ is preferably $C_1$-$C_6$-alkyl;
more preferably $C_1$-$C_4$-alkyl;
most preferably $CH_3$;

$R^2$ is preferably $C_1$-$C_6$-alkyl;
more preferably $C_1$-$C_4$-alkyl;
most preferably $CH_3$;

$R^3$ is preferably $C_1$-$C_6$-alkyl, aryl, 5- or 6-membered heteroaryl or aryl-$C_1$-$C_6$-alkyl, wherein the heteroaryl or aryl ring is
  unsubstituted, partially or fully halogenated, or substituted by one to five substituents selected from the group consisting of CN, $NO_2$, $C_1$-$C_6$-alkyl, $C_1$-$C_6$-haloalkyl, OH, $C_1$-$C_6$-alkoxy and $C_1$-$C_6$-haloalkoxy;
  particularly preferred unsubstituted, partially or fully halogenated or substituted by one $C_1$-$C_6$-alkyl group;
  especially preferred unsubstituted or substituted by one halogen atom or one $C_1$-$C_6$-alkyl group;
  more preferred unsubstituted, substituted by one chlorine atom or by one $CH_3$ group;
  most preferred unsubstituted;
  also most preferred substituted by one chlorine atom;
  also most preferred substituted by one $CH_3$ group;
  particularly preferred $C_1$-$C_6$-alkyl or aryl, wherein the aryl ring is
    unsubstituted, partially or fully halogenated, or substituted by one to five substituents selected from the group consisting of CN, $NO_2$, $C_1$-$C_6$-alkyl, $C_1$-$C_6$-haloalkyl, OH, $C_1$-$C_6$-alkoxy and $C_1$-$C_6$-haloalkoxy;
    particularly preferred unsubstituted, partially or fully halogenated or substituted by one $C_1$-$C_6$-alkyl group;
    especially preferred unsubstituted or substituted by one halogen atom or one $C_1$-$C_6$-alkyl group;
    more preferred unsubstituted, substituted by one chlorine atom or by one $CH_3$ group;
    most preferred unsubstituted;
    also most preferred substituted by one chlorine atom;
    also most preferred substituted by one $CH_3$ group;
  also particularly preferred aryl or aryl-$C_1$-$C_6$-alkyl, wherein the aryl ring is
    unsubstituted, partially or fully halogenated, or substituted by one to five substituents selected from the group consisting of CN, $NO_2$, $C_1$-$C_6$-alkyl, $C_1$-$C_6$-haloalkyl, OH, $C_1$-$C_6$-alkoxy and $C_1$-$C_6$-haloalkoxy;
    particularly preferred unsubstituted, partially or fully halogenated or substituted by one $C_1$-$C_6$-alkyl group;
    especially preferred unsubstituted or substituted by one halogen atom or one $C_1$-$C_6$-alkyl group;
    more preferred unsubstituted, substituted by one chlorine atom or by one $CH_3$ group;
    most preferred unsubstituted;
    also most preferred substituted by one chlorine atom;
    also most preferred substituted by one $CH_3$ group;
  also particularly preferred $C_1$-$C_6$-alkyl or aryl-$C_1$-$C_6$-alkyl, wherein the aryl ring is
    unsubstituted, partially or fully halogenated, or substituted by one to five substituents selected from the group consisting of CN, $NO_2$, $C_1$-$C_6$-alkyl, $C_1$-$C_6$-haloalkyl, OH, $C_1$-$C_6$-alkoxy and $C_1$-$C_6$-haloalkoxy;
    particularly preferred unsubstituted, partially or fully halogenated or substituted by one $C_1$-$C_6$-alkyl group;
    especially preferred unsubstituted or substituted by one halogen atom or one $C_1$-$C_6$-alkyl group;
    more preferred unsubstituted, substituted by one chlorine atom or by one $CH_3$ group;
    most preferred unsubstituted;
    also most preferred substituted by one chlorine atom;
    also most preferred substituted by one $CH_3$ group;
  especially preferred $C_1$-$C_6$-alkyl;
  more preferred $CH_3$;
  also especially preferred aryl, wherein the aryl ring is
    unsubstituted, partially or fully halogenated, or substituted by one to five substituents selected from the group consisting of CN, $NO_2$, $C_1$-$C_6$-alkyl, $C_1$-$C_6$-haloalkyl, OH, $C_1$-$C_6$-alkoxy and $C_1$-$C_6$-haloalkoxy;
    particularly preferred unsubstituted, partially or fully halogenated or substituted by one $C_1$-$C_6$-alkyl group;
    especially preferred unsubstituted or substituted by one halogen atom or one $C_1$-$C_6$-alkyl group;
    more preferred unsubstituted, substituted by one chlorine atom or by one $CH_3$ group;
    most preferred unsubstituted;
    also most preferred substituted by one chlorine atom;
    also most preferred substituted by one $CH_3$ group;
  also especially preferred aryl-$C_1$-$C_6$-alkyl, wherein the aryl-$C_1$-$C_6$-alkyl ring is
    unsubstituted, partially or fully halogenated, or substituted by one to five substituents selected from the group consisting of CN, $NO_2$, $C_1$-$C_6$-alkyl, $C_1$-$C_6$-haloalkyl, OH, $C_1$-$C_6$-alkoxy and $C_1$-$C_6$-haloalkoxy;
    particularly preferred unsubstituted, partially or fully halogenated or substituted by one $C_1$-$C_6$-alkyl group;
    especially preferred unsubstituted or substituted by one halogen atom or one $C_1$-$C_6$-alkyl group;
    more preferred unsubstituted, substituted by one chlorine atom or by one $CH_3$ group;
    most preferred unsubstituted;
    also most preferred substituted by one chlorine atom;
    also most preferred substituted by one $CH_3$ group;
$R^3$ is also preferably $C_1$-$C_6$-alkyl, phenyl or benzyl,
  more preferably methyl, ethyl, phenyl or benzyl,
  especially preferably methyl, phenyl or benzyl,
  wherein the phenyl or the benzyl ring is
    unsubstituted, partially or fully halogenated or substituted by one $C_1$-$C_6$-alkyl group, particularly preferred unsubstituted or substituted by one halogen atom or one $C_1$-$C_6$-alkyl group;
    especially preferred unsubstituted, substituted by one chlorine atom or by one $CH_3$ group;
    more preferred unsubstituted;
    also more preferred substituted by one chlorine atom,
    also more preferred substituted by one $CH_3$ group;
  particularly preferred $C_1$-$C_6$-alkyl or phenyl, wherein the phenyl ring is
    unsubstituted, partially or fully halogenated or substituted by one $C_1$-$C_6$-alkyl group,
    particularly preferred unsubstituted or substituted by one halogen atom or one $C_1$-$C_6$-alkyl group;
    especially preferred unsubstituted, substituted by one chlorine atom or by one $CH_3$ group;
    more preferred unsubstituted;
    also more preferred substituted by one chlorine atom,
    also more preferred substituted by one $CH_3$ group;
  also particularly preferred phenyl or benzyl, wherein the phenyl or the benzyl ring is
    unsubstituted, partially or fully halogenated or substituted by one $C_1$-$C_6$-alkyl group,
    particularly preferred unsubstituted or substituted by one halogen atom or one $C_1$-$C_6$-alkyl group;
    especially preferred unsubstituted, substituted by one chlorine atom or by one $CH_3$ group;
    more preferred unsubstituted;
    also more preferred substituted by one chlorine atom,
    also more preferred substituted by one $CH_3$ group;
  also particularly preferred $C_1$-$C_6$-alkyl or benzyl, wherein the benzyl ring is
    unsubstituted, partially or fully halogenated or substituted by one $C_1$-$C_6$-alkyl group,
    particularly preferred unsubstituted or substituted by one halogen atom or one $C_1$-$C_6$-alkyl group;

especially preferred unsubstituted, substituted by one chlorine atom or by one CH₃ group;
more preferred unsubstituted;
also more preferred substituted by one chlorine atom,
also more preferred substituted by one CH₃ group;
especially preferred phenyl, wherein the phenyl ring is
unsubstituted, partially or fully halogenated or substituted by one $C_1$-$C_6$-alkyl group,
particularly preferred unsubstituted or substituted by one halogen atom or one $C_1$-$C_6$-alkyl group;
especially preferred unsubstituted, substituted by one chlorine atom or by one CH₃ group;
more preferred unsubstituted;
also more preferred substituted by one chlorine atom,
also more preferred substituted by one CH₃ group;
Z is preferably O,
is also preferably S.

Particular preference is also given to carbamates of formulae (I.1) to (I.8) of Table A listed below, in which the variables $R^1$, $R^2$, $R^3$ and Z together have the meanings given in one row of Table A (carbamates of formulae I.1 to I.8); and where the definitions of the variables $R^1$, $R^2$, $R^3$ and Z are of particular importance for the compounds according to the invention not only in combination with one another but in each case also on their own:

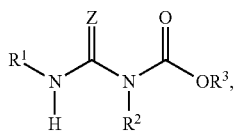

(I)

TABLE A

| No. | $R^1$ | $R^2$ | $R^3$ | Z |
|---|---|---|---|---|
| I.1. | CH₃ | CH₃ | CH₃ | O |
| I.2. | CH₃ | CH₃ | C₂H₅ | O |
| I.3. | CH₃ | CH₃ | C₆H₅ | O |
| I.4. | CH₃ | CH₃ | CH₂—C₆H₅ | O |
| I.5. | CH₃ | CH₃ | CH₃ | S |
| I.6. | CH₃ | CH₃ | C₂H₅ | S |
| I.7. | CH₃ | CH₃ | C₆H₅ | S |
| I.8. | CH₃ | CH₃ | CH₂—C₆H₅ | S |

More particular preference is given to the carbamates of formulae (I.5) and (I.7) as defined above:

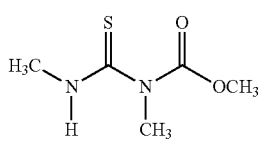

(I.5)

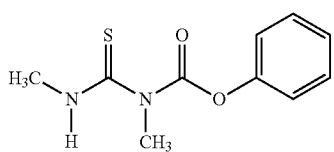

(I.7)

Very particular preference is given to the carbamate of formula (I.5) as defined above. Also very particular preference is given to the carbamate of formula (I.7) as defined above.

Carbamates of formula (I) can be prepared by reacting (thio)urea compounds of formula (II),

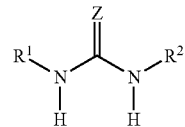

(II)

wherein $R^1$, $R^2$ and Z are defined as in formula (I);
with chloroformic acid esters of formula (III)

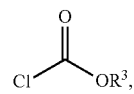

(III)

wherein $R^3$ is defined as in formula (I);
in the presence of a base.

The reaction of the (thio)urea compounds of formula (II) with the chloroformic acid ester of formula (III), in the presence a base is generally carried out at a temperature in the range from −10 to 130° C., preferably in the range from 15 to 110° C., more preferably in the range from 20 to 80° C.

In one embodiment of the process according to the invention, the chloroformic acid esters of formula (III) are used in excess with regard to the (thio)urea compounds of formula (II).

In another embodiment of the process according to the invention, the chloroformic acid esters of formula (III) and the (thio)urea compound of formula (II) are used in equimolar amounts.

In another embodiment of the process according to the invention, the (thio)urea compounds of formula (II) are used in excess with regard to the chloroformic acid esters of formula (III).

Preferably the molar ratio of the chloroformic acid esters of formula (III) to the (thio)urea compound of formula (II) is in the range from 0.9:1 to 1.5:1, preferably from 1.05:1 to 1.15:1, especially preferred 1.1:1, more preferred 1.05:1.

The reaction of the (thio)urea compounds of formula (II) with the chloroformic acid ester of formula (III) is carried out in the presence of a base.

Examples of suitable bases include metal-containing bases and nitrogen-containing bases.

Examples of suitable metal-containing bases are inorganic compounds such as alkali metal and alkaline earth metal hydroxides, and other metal hydroxides, such as lithium hydroxide, sodium hydroxide, potassium hydroxide, magnesium hydroxide, calcium hydroxide and aluminum hydroxide; alkali metal and alkaline earth metal oxide, and other metal oxides, such as lithium oxide, sodium oxide, potassium oxide, magnesium oxide, calcium oxide and magnesium oxide, iron oxide, silver oxide; alkali metal and alkaline earth metal hydrides such as lithium hydride, sodium hydride, potassium hydride and calcium hydride, alkali metal amides such as lithium amide, sodium amide and potassium amide; alkali metal and alkaline earth metal acetates such as lithium acetate, sodium acetate, potassium acetate, magnesium acetate, and calcium acetate; alkali metal and alkaline earth metal carbonates such as lithium carbonate, sodium carbonate, potassium carbonate, magnesium carbonate, and calcium carbonate, as well as alkali metal hydrogen carbonates (bicarbonates) such as lithium hydrogen carbonate, sodium hydrogen carbonate, potassium hydrogen carbonate; alkali metal and alkaline earth metal phosphates such as potassium phosphate, calcium phosphate; metal organic compounds, preferably alkali metal alkyls such as methyl lithium, butyl lithium and phenyl lithium, alkyl magnesium halides such as methyl magnesium chloride and isopropyl magnesium chloride, as well as alkali metal and alkaline earth metal alkoxides such as sodium methoxide, sodium ethoxide, potassium ethoxide, potassium tert-butoxide, potassium tert-pentoxide and dimethoxymagnesium; and furthermore organic bases, such as tertiary amines such as trimethylamine, triethylamine, diisopropylethylamine and N-methylpiperidine, pyridine, substituted pyridines such as collidine, lutidine, N-methylmorpholine and 4-dimethylaminopyridine and also bicyclic amines.

Examples of suitable nitrogen-containing bases are $C_1$-$C_6$-alkylamines, preferably trialkylamines, for example triethylamine, trimethylamine, N-ethyldiisopropylamine; pyridine, lutidine, collidine, 4-(dimethylamino)pyridine (DMAP), imidazole, 1,8-diazabicyclo[5.4.0]undec-7-ene (DBU) or 1,5-diazabicyclo[4.3.0]non-5-ene (DBN).

Preferred bases are alkali metal and alkaline earth metal carbonates, alkali metal hydrogen carbonates (bicarbonates) and $C_1$-$C_6$-alkylamines.

Especially preferred bases are alkali metal and alkaline earth metal carbonates and alkali metal hydrogen carbonates (bicarbonates).

The term base as used herein also includes mixtures of two or more, preferably two of the above compounds. Particular preference is given to the use of one base.

The bases are generally employed in equimolar amounts, however they can also be employed in understochiometric amounts, in excess or, if appropriate, be used as solvent.

Preferably the bases are used in excess, more preferably the ratio of the (thio)urea compound (II) to the base is in the range from 1:2, preferably from 1:1.8, particularly preferred 1:1.1 mole equivalents based on the (thio)urea compound of the formula (II).

It may be advantageous to add the base offset over a period of time.

The reaction of the (thio)urea compounds of formula (II) with the chloroformic acid esters of formula (III) and a base is carried out in a solvent. Suitable in principle are all solvents which are capable of dissolving the (thio)urea compounds of formula (II) and the chloroformic acid esters of formula (III) at least partly and preferably fully under the reaction conditions.

Examples of suitable solvents are aliphatic hydrocarbons such as pentane, hexane, cyclohexane, nitromethane and mixtures of $C_5$-$C_8$-alkanes; aromatic hydrocarbons such as benzene, chlorobenzene, toluene, cresols, o-, m- and p-xylene; halogenated hydrocarbons such as dichloromethane, 1,2-dichloroethane, chloroform, carbon tetrachloride and chlorobenzene; ethers such as diethyl ether, diisopropyl ether, tert.-butyl methylether (TBME), dioxane, anisole and tetrahydrofuran (THF); esters such as ethyl acetate and butyl acetate; nitriles such as acetonitrile and propionitrile; ketones such as acetone, methyl ethyl ketone, diethyl ketone, tert-butyl methyl ketone, cyclohexanone; as well as dipolar aprotic solvents such as sulfolane, dimethyl-sulfoxide, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are ethers, aromatic hydrocarbons, nitriles and esters as defined above. Particularly preferred solvents are THF, toluene, acetonitrile, ethyl acetate and butyl acetate.

The term solvent as used herein also includes mixtures of two or more of the above solvents.

For the reaction, the (thio)urea compounds of formula (II), the chloroformic acid esters of formula (III) and the base may be contacted with one another in any desired manner, i.e. the reactants and the base may be introduced into the reaction vessel separately, simultaneously or successively and reacted. For example, the (thio)urea compounds of formula (II) and the chloroformic acid esters of formula (III) may be initially charged in a reaction vessel, if appropriate with the desired solvent, and then the desired reaction conditions may be attained. However, it is also possible to introduce the majority or entirety of the (thio)urea compounds of formula (II) and subsequently add the chloroformic acid esters of formula (III), if appropriate in a solvent, under reaction conditions, into the reaction vessel.

It might be advantageous, to add the base a little at a time.

In one embodiment of the process according to the invention, the chloroformic acid esters of formula (III) and the base are initially charged in a reaction vessel, if appropriate with the desired solvent, and subsequently the (thio)urea compounds of formula (II) are added, more preferably are added a little at a time, into the reaction vessel.

In a preferred embodiment of the process according to the invention, the (thio)urea compounds of formula (II) and the base are initially charged in a reaction vessel, if appropriate with the desired solvent, and subsequently the chloroformic acid esters of formula (III) are added, more preferably are added a little at a time, into the reaction vessel.

Such embodiment is particularly preferred in case $R^3$ within the chloroformic acid esters of formula (III) is $C_1$-$C_6$-alkyl, especially preferred methyl.

In a further preferred embodiment of the invention, the majority, in particular at least 80% and more preferably the entirety or virtually the entirety (>95%) of the (thio)urea compounds of formula (II) and the base are initially charged, and the majority, in particular at least 80% and more preferably the entirety or virtually the entirety (>95%) of the chloroformic acid esters of formula (III) is added thereto under reaction conditions in the course of the reaction, for example over a period from 0.5 to 20 h and in particular from 1 to 10 h. To this end, the chloroformic acid esters of formula (III) will preferably be dissolved in a solvent.

In another preferred embodiment of the process according to the invention, the (thio)urea compounds of formula (II) and the chloroformic acid esters of formula (III) are initially charged in a reaction vessel, if appropriate with the desired solvent, and subsequently the base is added into the reaction vessel; more preferably is added into the reaction vessel a little at a time.

Such embodiment is particularly preferred in case $R^3$ within the chloroformic acid esters of formula (III) is aryl, especially preferred phenyl.

In a further preferred embodiment of the invention, the (thio)urea compounds of formula (II) and the chloroformic acid esters of formula (III) are initially charged and then the majority, in particular at least 80% and more preferably the entirety or virtually the entirety (>95%), of the base is added thereto. The reaction may if appropriate be completed by metering in further base.

The reaction can be carried out at atmospheric pressure, reduced pressure or under elevated pressure, if appropriate under an inert gas, continuously or batchwise.

After completion or partial completion of the reaction, the reaction mixture can be worked up by the methods customary for the purpose by means of standard techniques. Examples thereof include filtration, aqueous work-up, and evaporation of solvents and/or other volatile compounds. These methods can also be combined with each other.

In general the solvent used is removed by customary methods, distillatively for example. The crude product can then be taken up in a non-water-miscible organic solvent, any impurities extracted with unacidified or acidified water, and the system can then be dried and the solvent removed under reduced pressure.

For further purification it is possible to employ the typical methods such as crystallization, precipitation (for example by addition of an apolar solvent such as pentane, cyclohexane, heptane or toluene, or mixtures of said solvents) or chromatography.

The (thio)urea compounds of formula (II) necessary for the preparation of the carbamates of formula (I) are commercially available or can be prepared by methods known in the art.

(Thio)urea compounds of formula (II) can be prepared by reacting iso(thio)cyanates of formula (IV) with amines of formula (V):

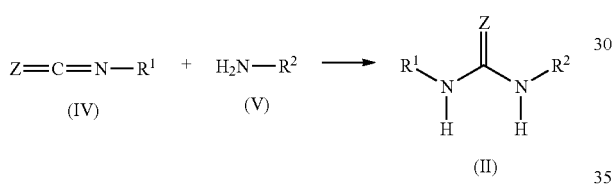

wherein $R^1$, $R^2$ and Z are as defined as in formula (I) above.

The reaction of iso(thio)cyanates of formula (IV) with amines of formula (V) is usually carried out at a temperature in the range from −10 to 130° C., preferably in the range from 15 to 110° C., more preferably in the range from 20 to 40° C. (e.g. G. Kaupp et al., Tetrahedron 56, 2000, pages 6899-6911).

The reaction of the iso(thio)cyanates of formula (IV) with amines of formula (V) is carried out in a solvent.

Examples of suitable solvents are aliphatic hydrocarbons such as pentane, hexane, cyclohexane, nitromethane and mixtures of $C_5$-$C_8$-alkanes; aromatic hydrocarbons such as benzene, chlorobenzene, toluene, cresols, o-, m- and p-xylene; halogenated hydrocarbons such as dichloromethane, 1,2-dichloroethane, chloroform, carbon tetrachloride and chlorobenzene; ethers such as diethyl ether, diisopropyl ether, tert.-butyl methylether (TBME), dioxane, anisole and tetrahydrofuran (THF); esters such as ethyl acetate and butyl acetate; nitriles such as acetonitrile and propionitrile; ketones such as acetone, methyl ethyl ketone, diethyl ketone, tert-butyl methyl ketone, cyclohexanone; as well as dipolar aprotic solvents such as sulfolane, dimethyl-sulfoxide, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are ethers, aromatic hydrocarbons, nitriles and esters as defined above. Particularly preferred solvents are THF, acetonitrile and ethyl acetate.

The term solvent as used herein also includes mixtures of two or more of the above solvents.

Work up can be carried out in a known manner.

The iso(thio)cyanates of formula (IV) required for the preparation of the (thio)urea compounds of formula (II) are commercially available.

The amines of formula (V) required for the preparation of the (thio)urea compounds of formula (II) are commercially available.

Accordingly, in a further preferred embodiment of the process of the invention carbamates of formula (I), are prepared by a) reacting iso(thio)cyanates of formula (IV) with amines of formula (V) to give (thio)urea compounds of formula (II); and b) reacting the (thio)urea compounds of formula (II) with chloroformic acid esters of formula (III) to give carbamates of formula (I):

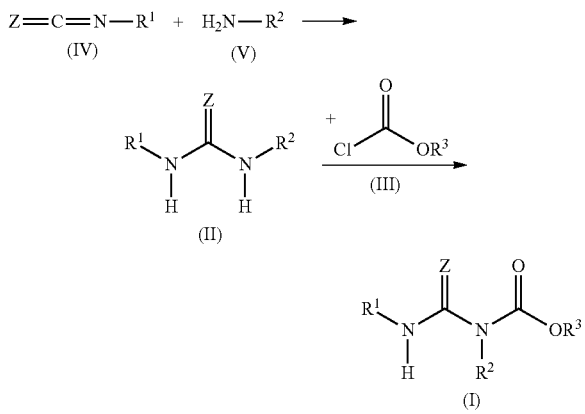

In one embodiment of the present invention the (thio)urea compounds of formula (II) are isolated prior to be used in step b), wherein the (thio)urea compounds of formula (II) are reacted with chloroformic acid esters of formula (III) to give carbamates of formula (I) as described above.

In another embodiment the (thio)urea compounds of formula (II) are not isolated, and the reaction mixture obtained in step a) is directly used in step b) and reacted with chloroformic acid esters of formula (III) to give carbamates of formula (I) as described above.

Accordingly, in a further preferred embodiment of the process of the invention carbamates of formula (I), are prepared by a) reacting iso(thio)cyanates of formula (IV) with amines of formula (V); and b) reacting the reaction mixture resulting from step a) with chloroformic acid esters of formula (III) to give carbamates of formula (I).

The chloroformic acid esters of formula (III) necessary for the preparation of the carbamates of formula (II) are commercially available.

The carbamates of formula (I) are useful in the synthesis of benzoxazinones of formula (VII), which are herbicidal active ingredients as described in WO 10/145992.

Benzoxazinones of formula (VII) can be prepared by reacting carbamates of formula (I) with carbamat-benzoxazinones of formula (VI) in the presence of a base:

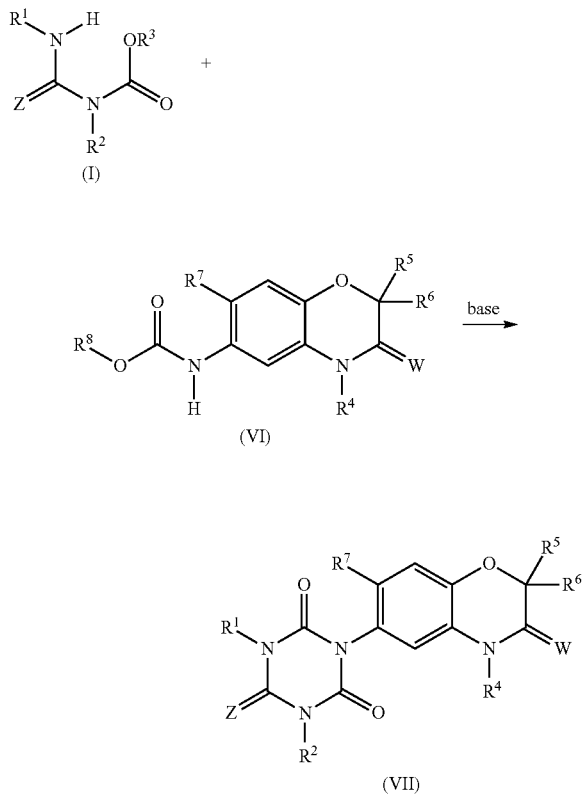

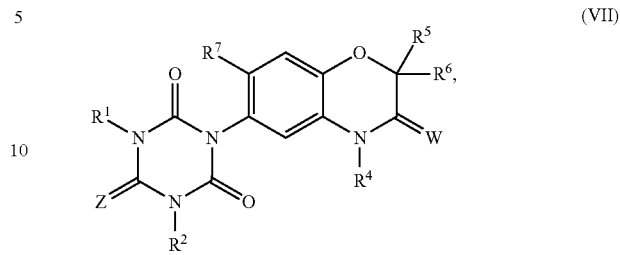

wherein

R$^1$, R$^2$, R$^3$ and Z have the meanings, preferably the preferred meanings, as defined in formula (I) above;

R$^4$ is H, C$_1$-C$_6$-alkyl, C$_1$-C$_6$-haloalkyl, C$_3$-C$_6$-cycloalkyl, C$_3$-C$_6$-alkenyl, C$_3$-C$_6$-haloalkenyl, C$_3$-C$_6$-alkynyl, C$_3$-C$_6$-haloalkynyl, C$_1$-C$_6$-alkoxy or C$_3$-C$_6$-cycloalkyl-C$_1$-C$_6$-alkyl;

R$^5$ is H, halogen or C$_1$-C$_6$-alkyl;

R$^6$ is H, halogen or C$_1$-C$_6$-alkyl;

R$^7$ is H, halogen or C$_1$-C$_6$-alkyl; and

R$^8$ is C$_1$-C$_6$-haloalkyl, C$_1$-C$_6$-cyanoalkyl, C$_1$-C$_6$-nitroalkyl, aryl, 5- or 6-membered heteroaryl or aryl-C$_1$-C$_6$-alkyl, wherein the aryl or heteroaryl rings are unsubstituted, partially or fully halogenated, or substituted by one to five substituents selected from the group consisting of CN, NO$_2$, C$_1$-C$_6$-alkyl, C$_1$-C$_6$-haloalkyl, OH, C$_1$-C$_6$-alkoxy, C$_1$-C$_6$-haloalkoxy, formyl, C$_1$-C$_6$-alkylcarbonyl, hydroxycarbonyl, and C$_1$-C$_6$-alkoxycarbonyl; and W is O or S.

Accordingly, in a further preferred embodiment of the invention the carbamates of formula (I) are used for the manufacturing of benzoxazinones of formula (VII) by reacting the carbamates of formula (I) with carbamat-benzoxazinones of formula (VI) to give benzoxazinones of formula (VII).

With respect to the substituents within the benzoxazinones of formula (VII), the particularly preferred embodiments of the benzoxazinones of formula (VII) correspond, either independently of one another or in combination with one another, to those of the substituents of R$^1$, R$^2$ and Z of formula (I); and R$^4$ is preferably C$_3$-C$_6$-alkynyl or C$_3$-C$_6$-haloalkynyl, more preferably C$_3$-alkynyl or C$_3$-haloalkynyl, particularly preferred CH$_2$C≡CH, CH$_2$C≡CCl or CH$_2$C≡CBr;

is also preferably C$_3$-C$_6$-alkynyl or C$_3$-C$_6$-cycloalkyl-C$_1$-C$_6$-alkyl, particularly preferred propargyl or cyclopropylmethyl;

is also preferably C$_3$-C$_6$-alkynyl, more preferably C$_3$-alkynyl; particularly preferred CH$_2$C≡CH;

is also preferably C$_3$-C$_6$-halolkynyl, more preferably C$_3$-halolkynyl, particularly preferred CH$_2$C≡CCl or CH$_2$C≡CBr;

R$^5$ is preferably halogen; particularly preferred Cl or F; especially preferred F;

R$^6$ is preferably H, Cl or F; particularly preferred H or F, especially preferred H;

is also preferably halogen, particularly preferred F or Cl, especially preferred F;

R$^7$ is preferably H or F; particularly preferred H;

is also preferably halogen; particularly preferred F or Cl; especially preferred F;

W is preferably O, is also preferably S.

Particular preference is also given to the preparation of benzoxazinones of formula (VII.a), which correspond to benzoxazinones of formula (VII) wherein R$^5$ is F, R$^1$ and R$^1$ are CH$_3$, W is O and Z is S:

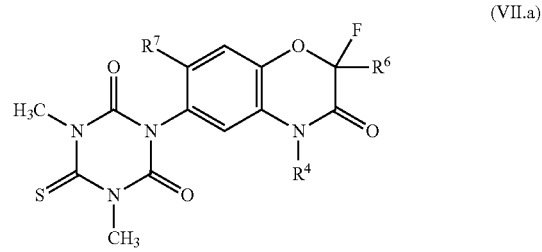

wherein the variables R$^4$, R$^6$ and R$^7$ have the meanings, in particular the preferred meanings, as defined above;

most preference to the preparation of benzoxazinones of formulae (VII.a.1) to (VII.a.54) of Table B listed below, in which the variables R$^4$, R$^6$ and R$^7$ together have the meanings given in one row of Table A (benzoxazinones of formulae VII.a.1 to VII.a.54); and where the definitions of the variables R$^4$, R$^6$ and R$^7$ are of particular importance for the process and the compounds according to the invention not only in combination with one another but in each case also on their own:

TABLE B

| No. | $R^4$ | $R^6$ | $R^7$ |
|---|---|---|---|
| VII.a.1 | H | H | H |
| VII.a.2 | $CH_3$ | H | H |
| VII.a.3 | $C_2H_5$ | H | H |
| VII.a.4 | $CH_2$—$C_2H_5$ | H | H |
| VII.a.5 | $CH(CH_3)_2$ | H | H |
| VII.a.6 | $CH_2$—$CH_2$—$(CH_3)_2$ | H | H |
| VII.a.7 | $CH_2$—$CH$=$CH_2$ | H | H |
| VII.a.8 | $CH_2C$≡$CH$ | H | H |
| VII.a.9 | $CH_2C$≡$C$—Br | H | H |
| VII.a.10 | H | F | H |
| VII.a.11 | $CH_3$ | F | H |
| VII.a.12 | $C_2H_5$ | F | H |
| VII.a.13 | $CH_2$—$C_2H_5$ | F | H |
| VII.a.14 | $CH(CH_3)_2$ | F | H |
| VII.a.15 | $CH_2$—$CH_2$—$(CH_3)_2$ | F | H |
| VII.a.16 | $CH_2$—$CH$=$CH_2$ | F | H |
| VII.a.17 | $CH_2C$≡$CH$ | F | H |
| VII.a.18 | $CH_2C$≡$C$—Br | F | H |
| VII.a.19 | H | H | F |
| VII.a.20 | $CH_3$ | H | F |
| VII.a.21 | $C_2H_5$ | H | F |
| VII.a.22 | $CH_2$—$C_2H_5$ | H | F |
| VII.a.23 | $CH(CH_3)_2$ | H | F |
| VII.a.24 | $CH_2$—$CH_2$—$(CH_3)_2$ | H | F |
| VII.a.25 | $CH_2$—$CH$=$CH_2$ | H | F |
| VII.a.26 | $CH_2C$≡$CH$ | H | F |
| VII.a.27 | $CH_2C$≡$C$—Br | H | F |
| VII.a.28 | H | F | F |
| VII.a.29 | $CH_3$ | F | F |
| VII.a.30 | $C_2H_5$ | F | F |
| VII.a.31 | $CH_2$—$C_2H_5$ | F | F |
| VII.a.32 | $CH(CH_3)_2$ | F | F |
| VII.a.33 | $CH_2$—$CH_2$—$(CH_3)_2$ | F | F |
| VII.a.34 | $CH_2$—$CH$=$CH_2$ | F | F |
| VII.a.35 | $CH_2C$≡$CH$ | F | F |
| VII.a.36 | $CH_2C$≡$C$—Br | F | F |
| VII.a.37 | H | H | Cl |
| VII.a.38 | $CH_3$ | H | Cl |
| VII.a.39 | $C_2H_5$ | H | Cl |
| VII.a.40 | $CH_2$—$C_2H_5$ | H | Cl |
| VII.a.41 | $CH(CH_3)_2$ | H | Cl |
| VII.a.42 | $CH_2$—$CH_2$—$(CH_3)_2$ | H | Cl |
| VII.a.43 | $CH_2$—$CH$=$CH_2$ | H | Cl |
| VII.a.44 | $CH_2C$≡$CH$ | H | Cl |
| VII.a.45 | $CH_2C$≡$C$—Br | H | Cl |
| VII.a.46 | H | F | Cl |
| VII.a.47 | $CH_3$ | F | Cl |
| VII.a.48 | $C_2H_5$ | F | Cl |
| VII.a.49 | $CH_2$—$C_2H_5$ | F | Cl |
| VII.a.50 | $CH(CH_3)_2$ | F | Cl |
| VII.a.51 | $CH_2$—$CH_2$—$(CH_3)_2$ | F | Cl |
| VII.a.52 | $CH_2$—$CH$=$CH_2$ | F | Cl |
| VII.a.53 | $CH_2C$≡$CH$ | F | Cl |
| VII.a.54 | $CH_2C$≡$C$—Br | F | Cl |

More particular preference is given to the preparation of the benzoxazinones of formulae (VII.a.28) and (VII.a.35) as defined above:

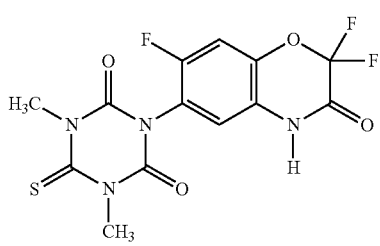
(VII.a.28)

Very particular preference is given to the preparation of the benzoxazinone of formula (VII.a.28) as defined above.

Also very particular preference is given to the preparation of the benzoxazinone of formula (VII.a.35) as defined above.

The reaction of the carbamates of formula (I) with the carbamat-benzoxazinones of formula (VI) in the presence of a base is generally carried out at a temperature in the range from −20° C. to the boiling point of the solvent used; preferably in the range from −20 to 150° C., particularly preferred in the range from 0 to 120° C., more preferably in the range from 20 to 80° C.

In one embodiment of the process according to the invention, the carbamates of formula (I) and the carbamat-benzoxazinones of formula (VI) are used in equimolar amounts.

In another embodiment of the process according to the invention, the carbamat-benzoxazinones of formula (VI) are used in excess with regard to the carbamates of formula (I).

In another embodiment of the process according to the invention, the carbamates of formula (I) are used in excess with regard to the carbamat-benzoxazinones of formula (VI). This embodiment is preferred.

Preferably the molar ratio of the carbamates of formula (I) to the carbamat-benzoxazinones of formula (VI) is in the range from 1.5:1 to 1:0.9, preferably 1.1:1 to 1:0.9, especially preferred 1:0.9, also especially preferred 1:1.

The reaction of the carbamates of formula (I) with the carbamat-benzoxazinones of formula (VI) is carried out in the presence of a base.

Examples of suitable bases include metal-containing bases and nitrogen-containing bases.

Examples of suitable metal-containing bases are inorganic compounds such as alkali metal and alkaline earth metal hydroxides, and other metal hydroxides, such as lithium hydroxide, sodium hydroxide, potassium hydroxide, magnesium hydroxide, calcium hydroxide and aluminum hydroxide; alkali metal and alkaline earth metal oxide, and other metal oxides, such as lithium oxide, sodium oxide, potassium oxide, magnesium oxide, calcium oxide and magnesium oxide, iron oxide, silver oxide; alkali metal and alkaline earth metal hydrides such as lithium hydride, sodium hydride, potassium hydride and calcium hydride; alkali metal and alkaline earth metal formates, acetates and other metal salts of carboxylic acids, such as sodium formate, sodium benzoate, lithium acetate, sodium acetate, potassium acetate, magnesium acetate, and calcium acetate; alkali metal and alkaline earth metal carbonates such as lithium carbonate, sodium carbonate, potassium carbonate, magnesium carbonate, and calcium carbonate, as well as alkali metal hydrogen carbonates (bicarbonates) such as lithium hydrogen carbonate, sodium hydrogen carbonate, potassium hydrogen carbonate; alkali metal and alkaline earth metal phosphates such as sodium phosphate, potassium phosphate and calcium phosphate; alkali metal and alkaline earth metal aryloxides such as sodium phenolate and potassium phenolate; and furthermore organic bases, such as ammonia, tertiary amines like $C_1$-$C_6$- alkylamines, preferably trialkylamines, such as trimethylamine, triethylamine, diisopropylethylamine, N-ethyldiisopropylamine; and also N-methylpiperidine, 4-(dimethylamino)pyridine (DMAP), imidazole, pyridine, substituted pyridines such as collidine, lutidine, N-methylmorpholine and 4-dimethylaminopyridine and also bicyclic amines, such as 1,8-diazabicyclo[5.4.0]undec-7-ene (DBU) or 1,5-diazabicyclo[4.3.0]non-5-ene (DBN)

Preferred bases are alkali metal and alkaline earth metal aryloxides, alkali metal and alkaline earth metal carbonates and alkali metal and alkaline earth metal acetates as defined above.

Especially preferred bases are alkali metal and alkaline earth metal aryloxides, and alkali metal and alkaline earth metal acetates as defined above.

The term base as used herein also includes mixtures of two or more, preferably two of the above compounds. Particular preference is given to the use of one base.

The bases are generally employed in catalytic amounts based on the carbamat-benzoxazinones of formula (VI), however they can also be employed in equimolar amounts or in excess.

Preferably the amount of base is from 1.5 mole equivalents to catalytic amounts, more preferably from 0.3 to 0.01 mole equivalents, especially preferred from 0.3 to 0.1 mole equivalents based on the carbamat-benzoxazinones of formula (VI).

The reaction of the carbamates of formula (I) with the carbamat-benzoxazinones of formula (VI) and a base is usually carried out in a solvent. However the reaction in melt is possible in principle as well.

Suitable in principle are all solvents which are capable of dissolving the carbamates of formula (I) and the carbamat-benzoxazinones of formula (VI) at least partly and preferably fully under reaction conditions.

Examples of suitable solvents are aliphatic hydrocarbons such as pentane, hexane, cyclohexane, nitromethane and mixtures of $C_5$-$C_8$-alkanes, aromatic hydrocarbons such as benzene, chlorobenzene, toluene, cresols, o-, m- and p-xylene, halogenated hydrocarbons such as dichloromethane, 1,2-dichloroethane, chloroform, carbon tetrachloride and chlorobenzene, ethers such as diethyl ether, diisopropyl ether, tert.-butyl methylether (TBME), dioxane, anisole and tetrahydrofuran (THF), esters such as ethyl acetate and butyl acetate; nitriles such as acetonitrile and propionitrile, ketones such as acetone, methyl ethyl ketone, diethyl ketone, tert-butyl methyl ketone, cyclohexanone; dipolar aprotic solvents such as sulfolane, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are esters and dipolar aprotic solvents as described above.

More preferred solvents are ethyl acetate and DMF.

The term solvent as used herein also includes mixtures of two or more of the above compounds.

For the reaction, the carbamates of formula (I), the carbamates-benzoxazinones of formula (VI) and the base may be contacted with one another in any desired manner, i.e. the reactants and the base may be introduced into the reaction vessel separately, simultaneously or successively and reacted.

For example, the carbamates of formula (I) and the carbamates-benzoxazinones of formula (VI) may be initially charged in a reaction vessel, if appropriate with the desired solvent, and then the desired reaction conditions may be attained. However, it is also possible to introduce the majority or entirety of the carbamates of formula (I) and subsequently add the carbamates-benzoxazinones of formula (VI), if appropriate in a solvent, under reaction conditions, into the reaction vessel.

It might be advantageous, to add the base a little at a time.

In one embodiment of the process according to the invention, the carbamat-benzoxazinones of formula (VI) and the base are initially charged in a reaction vessel, if appropriate with the desired solvent, and subsequently the carbamates of formula (I) are added into the reaction vessel.

In a preferred embodiment of the process according to the invention, the carbamates of formula (I) and the base are initially charged in a reaction vessel, if appropriate with the desired solvent, and subsequently the carbamat-benzoxazinones of formula (VI) are added into the reaction vessel.

In a further particular embodiment of the process according to the invention, in case $R^3$ within the carbamate of formula (I) is $C_1$-$C_6$-alkyl, especially preferred methyl, the carbamates of formula (I) and the base are initially charged in a reaction vessel, if appropriate with the desired solvent, and subsequently the carbamat-benzoxazinones of formula (VI) are added, more preferably are added a little at a time, into the reaction vessel.

In a further preferred embodiment of the invention, the majority, in particular at least 80% and more preferably the entirety or virtually the entirety (>95%) of the carbamates of formula (I) and the base are initially charged, and the majority, in particular at least 80% and more preferably the entirety or virtually the entirety (>95%) of the carbamat-benzoxazinones of formula (VI) is added thereto under reaction conditions in the course of the reaction, for example over a period from 0.5 to 20 h and in particular from 1 to 10 h. To this end, the carbamat-benzoxazinones of formula (III) will preferably be dissolved in a solvent.

In another preferred embodiment of the process according to the invention, the carbamates of formula (I) and the carbamat-benzoxazinones of formula (VI) are initially charged in a reaction vessel, if appropriate with the desired solvent, and subsequently the base is added into the reaction vessel.

The reaction temperature within such preferred embodiment is preferably in the range from 0 to 120° C., more preferably in the range from 20 to 80° C.

Such embodiment is particularly preferred in case $R^3$ within the carbamate of formula (I) is aryl, especially preferred phenyl.

In a further preferred embodiment of the invention, the carbamates of formula (I) and the carbamates-benzoxazinones of formula (VI) are initially charged and then the majority, in particular at least 80% and more preferably the entirety or virtually the entirety (>95%), of the base is added thereto. The reaction may if appropriate be completed by metering in further base.

The reaction can be carried out at atmospheric pressure, reduced pressure or under elevated pressure, if appropriate under an inert gas, continuously or batch-wise.

Preference is given to partly or completely removing the compound $R^3O$—H formed in the course of the reaction of the carbamates of formula (I) with carbamat-benzoxazinones of formula (VI), especially when the compound $R^3O$—H is a $C_1$-$C_4$-alkanol such as methanol or ethanol. To this end, the reaction will be carried out in a manner known per se at a temperature and a pressure at which the compounds $R^3O$—H, if appropriate, are partly or completely distilled out of the reaction mixture, optionally as an azeotrope with the solvent.

If appropriate, fresh solvent can be introduced into the mixture for compensation or the solvent distilled off with the compounds $R^3O$—H can be recycled into the reaction after optional distillative depletion of the compounds $R^3O$—H.

For these reasons, it is advantageous when the solvent used has a boiling point of at least 10° C., in particular at least 30° C., above the boiling point of the compounds R³O—H formed in the reaction (each at atmospheric pressure).

Appropriately, the reaction of the carbamates of formula (I) with carbamat-benzoxazinones of formula (VI) is carried out in an apparatus which is equipped with at least one distillation or rectification apparatus, for example a distillation column, which firstly allows the compound R³O—H, if appropriate together with the solvent, to be distilled off and simultaneously enables removal and recycling of any solvent distilled off with the compound R³O—H.

After completion or partial completion of the reaction, the reaction mixture can be worked up by the methods customary for the purpose by means of standard techniques. Examples thereof include filtration, aqueous work-up, and evaporation of solvents and/or other volatile compounds. These methods can also be combined with each other.

In general the solvent used is removed by customary methods, distillatively for example. The crude product can then be taken up in a non-water-miscible organic solvent, any impurities extracted with unacidified or acidified water, and the system can then be dried and the solvent removed under reduced pressure.

For further purification it is possible to employ the typical methods such as crystallization, precipitation (for example by addition of an apolar solvent such as pentane, cyclohexane, heptane or toluene, or mixtures of said solvents) or chromatography.

In a preferred embodiment of the reaction, in case the reaction has been carried out in DMF, the reaction mixture will generally be concentrated and/or cooled and/or a precipitant will be added. Suitable precipitants are solvents in which the benzoxazinones of formula (I) dissolve only to a slight extent, if at all, at least at temperatures below 25° C.

These include in particular alcohols such as methanol, ethanol, n-propanol, isopropanol, n-butanol, isobutanol, tert.-butanol, water, and the like; or mixtures thereof;

preferably methanol, isobutanol and water, or mixtures thereof.

The precipitation or crystallization may be followed by further purification measures.

In another variant of the reaction in the process according to the invention and depending on the base used, after the ending of the reaction, it might be advantageous to dilute the reaction mixture by addition of water and/or acids, the pH of the aqueous phase being adjusted to pH in between 6 to 8, preferably pH=7.

Acids suitable for this purpose are organic acids and aqueous mineral acids known to the skilled worker, such as acetic acid, hydrochloric acid, sulfuric acid, nitric acid or phosphoric acid, for example.

The reaction mixture can then be worked up by the methods customary therefor. In general, the phases are separated and the solvent used will be removed by customary processes, for example by distillation. For further purification, the customary processes such as for example crystallization (for example also by addition of a nonpolar solvent such as pentane, cyclohexane, heptane or toluene, or mixtures of the solvents mentioned) can be employed.

With respect to the substituents within the carbamat-benzoxazinones of formula (VI),

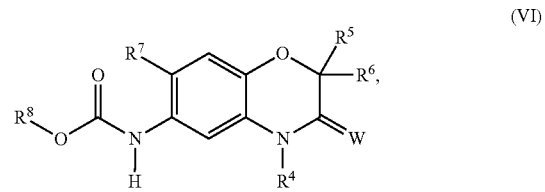

necessary for the use of the carbamates of formula (I) to prepare of benzoxazinones of formula (VII) according to the invention, the particularly preferred embodiments of the carbamat-benzoxazinones of formula (VI) correspond, either independently of one another or in combination with one another, to those of the variables of $R^4$, $R^5$, $R^6$, $R^7$ and W of the benzoxazinones of formula (VII), and $R^8$ is preferably $C_1$-$C_6$-haloalkyl, aryl, or aryl-$C_1$-$C_6$-alkyl,
  wherein the aryl ring is
    unsubstituted, partially or fully halogenated, or substituted by one to five substituents selected from the group consisting of CN, $NO_2$, $C_1$-$C_6$-alkyl, $C_1$-$C_6$-haloalkyl, OH, $C_1$-$C_6$-alkoxy and $C_1$-$C_6$-haloalkoxy;
    particularly preferred unsubstituted, partially or fully halogenated or substituted by one $C_1$-$C_6$-alkyl group;
    especially preferred unsubstituted or substituted by one halogen atom or one
    $C_1$-$C_6$-alkyl group;
    more preferred unsubstituted, substituted by one chlorine atom or by one $CH_3$ group;
    most preferred unsubstituted;
    also most preferred substituted by one chlorine atom;
    also most preferred substituted by one $CH_3$ group;
  particularly preferred $C_1$-$C_6$-haloalkyl or aryl,
  wherein the aryl ring is
    unsubstituted, partially or fully halogenated, or substituted by one to five substituents selected from the group consisting of CN, $NO_2$, $C_1$-$C_6$-alkyl, $C_1$-$C_6$-haloalkyl, OH, $C_1$-$C_6$-alkoxy and $C_1$-$C_6$-haloalkoxy;
    particularly preferred unsubstituted, partially or fully halogenated or substituted by one $C_1$-$C_6$-alkyl group;
    especially preferred unsubstituted or substituted by one halogen atom or one $C_1$-$C_6$-alkyl group;
    more preferred unsubstituted, substituted by one chlorine atom or by one $CH_3$ group;
    most preferred unsubstituted;
    also most preferred substituted by one chlorine atom;
    also most preferred substituted by one $CH_3$ group;
  especially preferred $C_1$-$C_6$-haloalkyl;
  also especially preferred aryl, wherein the aryl ring is
    unsubstituted, partially or fully halogenated, or substituted by one to five substituents selected from the group consisting of CN, $NO_2$, $C_1$-$C_6$-alkyl, $C_1$-$C_6$-haloalkyl, OH, $C_1$-$C_6$-alkoxy and $C_1$-$C_6$-haloalkoxy;
    particularly preferred unsubstituted, partially or fully halogenated or substituted by one $C_1$-$C_6$-alkyl group;
    especially preferred unsubstituted or substituted by one halogen atom or one $C_1$-$C_6$-alkyl group;
    more preferred unsubstituted, substituted by one chlorine atom or by one $CH_3$ group;
    most preferred unsubstituted;
    also most preferred substituted by one chlorine atom;
    also most preferred substituted by one $CH_3$ group;

more preferred phenyl, wherein the phenyl ring is
  unsubstituted, partially or fully halogenated, or substituted by one to five substituents selected from the group consisting of CN, NO$_2$, C$_1$-C$_6$-alkyl, C$_1$-C$_6$-haloalkyl, OH, C$_1$-C$_6$-alkoxy and C$_1$-C$_6$-haloalkoxy;
  particularly preferred unsubstituted, partially or fully halogenated or substituted by one C$_1$-C$_6$-alkyl group;
  especially preferred unsubstituted or substituted by one halogen atom or one C$_1$-C$_6$-alkyl group;
  more preferred unsubstituted, substituted by one chlorine atom or by one CH$_3$ group;
  most preferred unsubstituted;
  also most preferred substituted by one chlorine atom;
  also most preferred substituted by one CH$_3$ group;
also more preferred phenyl, wherein the phenyl ring is
  partially or fully halogenated, or substituted by one to five substituents selected from the group consisting of CN, NO$_2$, C$_1$-C$_6$-alkyl, C$_1$-C$_6$-haloalkyl, OH, C$_1$-C$_6$-alkoxy and C$_1$-C$_6$-haloalkoxy;
  particularly preferred partially or fully halogenated or substituted by one C$_1$-C$_6$-alkyl group;
  especially preferred substituted by one halogen atom or one C$_1$-C$_6$-alkyl group;
  more preferred substituted by one chlorine atom or by one CH$_3$ group.

Particular preference is given to the carbamat-benzoxazinones of formula (VI.a), which correspond to carbamat-benzoxazinones of formula (VI) wherein R$^5$ is F, R$^8$ is phenyl and W is O:

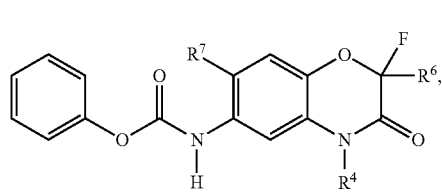

(VI.a)

wherein the variables R$^4$, R$^6$ and R$^7$ have the meanings, in particular the preferred meanings, as defined above;

special preference is given to the carbamat-benzoxazinones of formulae (VI.a.1) to (VI.a.54) of Table C listed below, in which the variables R$^4$, R$^6$ and R$^7$ together have the meanings given in one row of Table C (carbamat-benzoxazinones of formulae VI.a.1 to VI.a.54); and where the definitions of the variables R$^4$, R$^6$ and R$^7$ are of particular importance for the process according to the invention not only in combination with one another but in each case also on their own:

TABLE C

| No. | R$^4$ | R$^7$ | R$^6$ |
|---|---|---|---|
| VI.a.1 | H | H | H |
| VI.a.2 | CH$_3$ | H | H |
| VI.a.3 | C$_2$H$_5$ | H | H |
| VI.a.4 | CH$_2$—C$_2$H$_5$ | H | H |
| VI.a.5 | CH(CH$_3$)$_2$ | H | H |
| VI.a.6 | CH$_2$—CH$_2$—(CH$_3$)$_2$ | H | H |
| VI.a.7 | CH$_2$—CH=CH$_2$ | H | H |
| VI.a.8 | CH$_2$C≡CH | H | H |
| VI.a.9 | CH$_2$C≡C—Br | H | H |
| VI.a.10 | H | H | F |
| VI.a.11 | CH$_3$ | H | F |
| VI.a.12 | C$_2$H$_5$ | H | F |
| VI.a.13 | CH$_2$—C$_2$H$_5$ | H | F |
| VI.a.14 | CH(CH$_3$)$_2$ | H | F |
| VI.a.15 | CH$_2$—CH$_2$—(CH$_3$)$_2$ | H | F |
| VI.a.16 | CH$_2$—CH=CH$_2$ | H | F |
| VI.a.17 | CH$_2$C≡CH | H | F |
| VI.a.18 | CH$_2$C≡C—Br | H | F |
| VI.a.19 | H | F | H |
| VI.a.20 | CH$_3$ | F | H |
| VI.a.21 | C$_2$H$_5$ | F | H |
| VI.a.22 | CH$_2$—C$_2$H$_5$ | F | H |
| VI.a.23 | CH(CH$_3$)$_2$ | F | H |
| VI.a.24 | CH$_2$—CH$_2$—(CH$_3$)$_2$ | F | H |
| VI.a.25 | CH$_2$—CH=CH$_2$ | F | H |
| VI.a.26 | CH$_2$C≡CH | F | H |
| VI.a.27 | CH$_2$C≡C—Br | F | H |
| VI.a.28 | H | F | F |
| VI.a.29 | CH$_3$ | F | F |
| VI.a.30 | C$_2$H$_5$ | F | F |
| VI.a.31 | CH$_2$—C$_2$H$_5$ | F | F |
| VI.a.32 | CH(CH$_3$)$_2$ | F | F |
| VI.a.33 | CH$_2$—CH$_2$—(CH$_3$)$_2$ | F | F |
| VI.a.34 | CH$_2$—CH=CH$_2$ | F | F |
| VI.a.35 | CH$_2$C≡CH | F | F |
| VI.a.36 | CH$_2$C≡C—Br | F | F |
| VI.a.37 | H | Cl | H |
| VI.a.38 | CH$_3$ | Cl | H |
| VI.a.39 | C$_2$H$_5$ | Cl | H |
| VI.a.40 | CH$_2$—C$_2$H$_5$ | Cl | H |
| VI.a.41 | CH(CH$_3$)$_2$ | Cl | H |
| VI.a.42 | CH$_2$—CH$_2$—(CH$_3$)$_2$ | Cl | H |
| VI.a.43 | CH$_2$—CH=CH$_2$ | Cl | H |
| VI.a.44 | CH$_2$C≡CH | Cl | H |
| VI.a.45 | CH$_2$C≡C—Br | Cl | H |
| VI.a.46 | H | Cl | F |
| VI.a.47 | CH$_3$ | Cl | F |
| VI.a.48 | C$_2$H$_5$ | Cl | F |
| VI.a.49 | CH$_2$—C$_2$H$_5$ | Cl | F |
| VI.a.50 | CH(CH$_3$)$_2$ | Cl | F |
| VI.a.51 | CH$_2$—CH$_2$—(CH$_3$)$_2$ | Cl | F |
| VI.a.52 | CH$_2$—CH=CH$_2$ | Cl | F |
| VI.a.53 | CH$_2$C≡CH | Cl | F |
| VI.a.54 | CH$_2$C≡C—Br | Cl | F |

Also particularly preferred are the carbamat-benzoxazinones of formula VI.b, particularly preferred the carbamat-benzoxazinones of formulae VI.b.1 to VI.b.54, which differ from the corresponding carbamat-benzoxazinones of formulae VI.a.1 to VI.a.54 only in that R$^8$ is 4-chloro-phenyl:

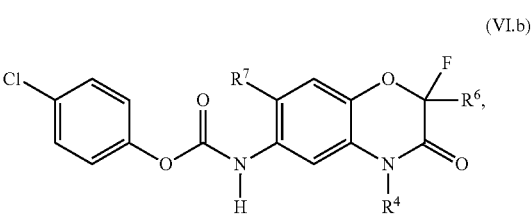

(VI.b)

Also particularly preferred are the carbamat-benzoxazinones of formula VI.c, particularly preferred the carbamat-benzoxazinones of formulae VI.c.1 to VI.c.54, which differ from the corresponding carbamat-benzoxazinones of formulae VI.a.1 to VI.a.54 only in that R$^8$ is 4-CH$_3$-phenyl:

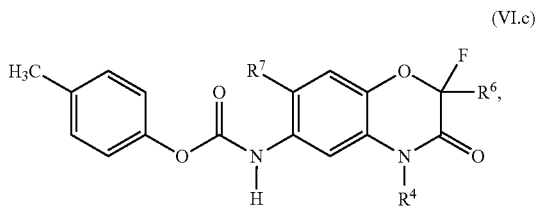
(VI.c)

Also particularly preferred are the carbamat-benzoxazinones of formula VI.d, particularly preferred the carbamat-benzoxazinones of formulae VI.d.1 to VI.d.54, which differ from the corresponding carbamat-benzoxazinones of formulae VI.a.1 to VI.a.54 only in that $R^8$ is 3-$CH_3$-phenyl:

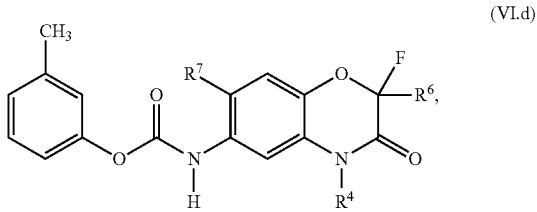
(VI.d)

Also particularly preferred are the carbamat-benzoxazinones of formula VI.e, particularly preferred the carbamat-benzoxazinones of formulae VI.e.1 to VI.e.54, which differ from the corresponding carbamat-benzoxazinones of formulae VI.a.1 to VI.a.54 only in that $R^8$ is 2-$CH_3$-phenyl:

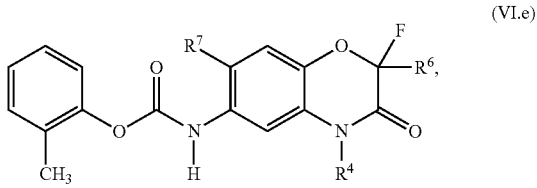
(VI.e)

More particular preference is given to the carbamat-benzoxazinones of formulae (VI.a.28) and (VI.a.35), as defined above:

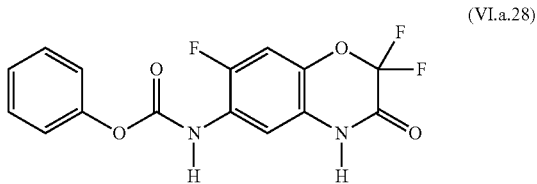
(VI.a.28)

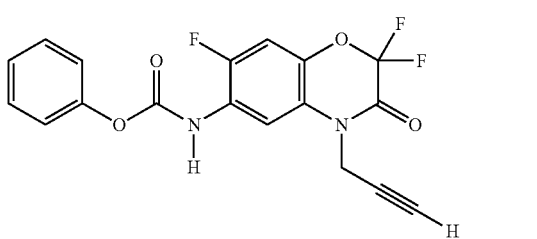
(VI.a.35)

Very particular preference is given to the carbamat-benzoxazinone of formula (VI.a.28). Also very particular preference is given to the carbamat-benzoxazinone of formula (IVI.a.35).

The carbamat-benzoxazinones of formula (VI) necessary for the use of the carbamates of formula (I) to prepare of benzoxazinones of formula (VII) can be prepared by reacting amino-benzoxazinones of formula (VIII) with compounds of formula (IX), optionally in the presence of a base:

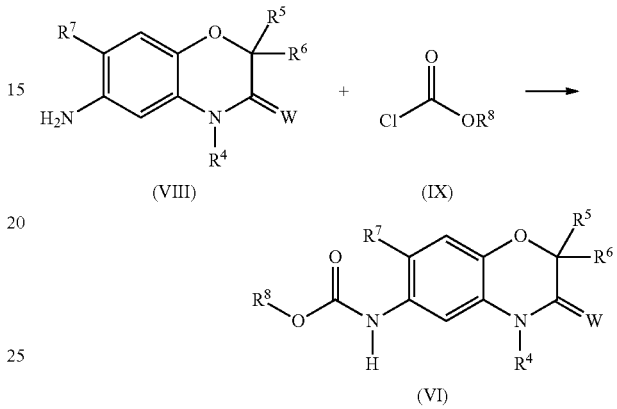

In case the reaction of the amino-benzoxazinones of formula (VIII) with compounds of formula (IX), is conducted in the presence of a base, the reaction is generally carried out at a temperature in the range from −40° C. to the boiling point of the solvent used, for example from −40 to 150° C., preferably in the range from −20 to 100° C., more preferably in the range from 0 to 70° C.

In case the reaction of the amino-benzoxazinones of formula (VIII) with compounds of formula (IX), is conducted in the absence of a base, the reaction is generally carried out at a temperature in the range from −40° C. to the boiling point of the solvent used, for example from −40 to 150° C., preferably in the range from 0 to 150° C., more preferably in the range from 50 to 130° C.

In case THF is used as the solvent, the reaction is preferably carried out at room temperature, i.e. at about 20° C.

In one embodiment of the process according to the invention, the compounds of formula (IX) are used in excess with regard to the amino-benzoxazinones of formula (VIII).

In another embodiment of the process according to the invention, the compounds of formula (IX) and the amino-benzoxazinones of formula (VIII) are used in equimolar amounts.

In another embodiment of the process according to the invention, the amino-benzoxazinones of formula (VIII) are used in excess with regard to the compounds of formula (IX).

Preferably the molar ratio of the compounds of formula (IX) to the amino-benzoxazinones of formula (VIII) is in the range from 0.9:1 to 1.5:1, preferably from 1.0:1 to 1.1.:1.

In one embodiment the reaction of the amino-benzoxazinone of formula (VIII) with the compounds of formula (IX) is carried out in the presence of a base.

Examples of suitable bases include metal-containing bases and nitrogen-containing bases. Examples of suitable metal-containing bases are inorganic compounds such as alkali metal and alkaline earth metal hydroxides, and other metal hydroxides, such as lithium hydroxide, sodium hydroxide, potassium hydroxide, magnesium hydroxide, calcium hydroxide and aluminum hydroxide; alkali metal and alkaline earth metal oxide, and other metal oxides, such as lithium oxide, sodium oxide, potassium oxide, magnesium oxide, calcium oxide and magnesium oxide, iron oxide, silver oxide; alkali metal and alkaline earth metal hydrides such as lithium hydride, sodium hydride, potassium hydride and calcium hydride; alkali metal and alkaline earth metal acetates such as lithium acetate, sodium acetate, potassium acetate, magnesium acetate, and calcium acetate; alkali metal and alkaline earth metal carbonates such as lithium carbonate, sodium carbonate, potassium carbonate, magnesium carbonate, and calcium carbonate, as well as alkali metal hydrogen carbonates (bicarbonates) such as lithium hydrogen carbonate, sodium hydrogen carbonate, potassium hydrogen carbonate; alkali metal and alkaline earth metal phosphates such as potassium phosphate, calcium phosphate; metal organic compounds, preferably alkali metal alkyls such as methyl lithium, butyl lithium and phenyl lithium; alkyl magnesium halides such as methyl magnesium chloride and isopropyl magnesium chloride as well as alkali metal and alkaline earth metal alkoxides such as sodium methoxide, sodium ethoxide, potassium ethoxide, potassium tert-butoxide, potassium tert-pentoxide and dimethoxymagnesium.

Examples of suitable nitrogen-containing bases are $C_1$-$C_6$-alkylamines, preferably trialkylamines, for example triethylamine, trimethylamine, N-ethyldiisopropylamine, ammonia, N-methylpiperidine, pyridine, substituted pyridines such as lutidine, collidine and 4-(dimethylamino)pyridine (DMAP), N-methylmorpholine, imidazole, 1,8-diazabicyclo[5.4.0]undec-7-ene (DBU) or 1,5-diazabicyclo[4.3.0]non-5-ene (DBN).

Preferred bases are tertiary amines and alkali metal and alkaline earth metal carbonates and bicarbonates as mentioned above.

Especially preferred bases are triethylamine and alkali metal and alkaline earth metal carbonates as mentioned above.

The term base as used herein also includes mixtures of two or more, preferably two of the above compounds. Particular preference is given to the use of one base.

The bases are generally employed in equimolar amounts; however they can also be employed in catalytic amounts, in excess or, if appropriate, be used as solvent.

In another embodiment the reaction of the amino-benzoxazinone of formula (VIII) with the compounds of formula (IX) is carried out in the absence of a base. Such embodiment is preferred.

The reaction may in principle be carried out in substance. However, preference is given to reacting the amino-benzoxazinones (VIII) with the compounds of formula (IX), and optionally a base, in an organic solvent. Suitable in principle are all solvents which are capable of dissolving the amino-benzoxazinones (VIII) and the compounds of formula (IX), and optionally a base at least partly and preferably fully under reaction conditions.

Examples of suitable solvents are aliphatic hydrocarbons such as pentane, hexane, cyclohexane, nitromethane and mixtures of $C_5$-$C_8$-alkanes; aromatic hydrocarbons such as benzene, chlorobenzene, toluene, cresols, o-, m- and p-xylene; halogenated hydrocarbons such as dichloromethane, 1,2-dichloroethane, chloroform, carbon tetrachloride and chlorobenzene; ethers such as diethyl ether, diisopropyl ether, tert.-butyl methylether (TBME), dioxane, anisole and tetrahydrofuran (THF); esters such as ethyl acetate and butyl acetate; nitriles such as acetonitrile and propionitrile; ketones such as acetone, methyl ethyl ketone, diethyl ketone, tert-butyl methyl ketone, cyclohexanone; as well as dipolar aprotic solvents such as sulfolane, dimethyl-sulfoxide, N,N-dimethylformamide (DMF), N,N-dimethylacetamide (DMAC), 1,3-dimethyl-2-imidazolidinone (DMI), N,N'-dimethylpropylene urea (DMPU), dimethyl sulfoxide (DMSO) and 1-methyl-2 pyrrolidinone (NMP).

Preferred solvents are ethers, esters, aromatic hydrocarbons and nitriles as described above. Particularly preferred solvents are THF, ethyl acetate, toluene and acetonitrile.

Especially preferred solvents are ethyl acetate and toluene.

The term solvent as used herein also includes mixtures of two or more of the above solvents.

For the reaction, the amino-benzoxazinones of formula (VIII), the compounds of formula (IX) and optionally the base may be contacted with one another in any desired manner, i.e. the reactants and optionally the base may be introduced into the reaction vessel separately, simultaneously or successively and reacted. For example, the amino-benzoxazinones of formula (VIII) and the compounds of formula (IX) may be initially charged in a reaction vessel, if appropriate with the desired solvent, and then the desired reaction conditions may be attained. However, it is also possible to introduce the majority or entirety of the amino-benzoxazinones of formula (VIII) and subsequently add the compounds of formula (IX), if appropriate in a solvent, under reaction conditions, into the reaction vessel.

In one embodiment of the process according to the invention, the compounds of formula (IX) and optionally the base are initially charged in a reaction vessel, if appropriate with the desired solvent, and subsequently the amino-benzoxazinones of formula (VIII) are added, more preferably are added a little at a time, into the reaction vessel.

In another embodiment of the process according to the invention, the amino-benzoxazinones of formula (VIII) and optionally the base are initially charged in a reaction vessel, if appropriate with the desired solvent, and subsequently the compounds of formula (IX) are added, more preferably are added a little at a time, into the reaction vessel. Such embodiment is preferred.

In a further preferred embodiment of the invention, the majority, in particular at least 80% and more preferably the entirety or virtually the entirety (>95%) of the amino-benzoxazinones of formula (VIII) and optionally the base are initially charged, and the majority, in particular at least 80% and more preferably the entirety or virtually the entirety (>95%) of the compounds of formula (IX) is added thereto under reaction conditions in the course of the reaction, for example over a period of from 0.5 to 20 h and in particular from 1 to 10 h. To this end, the compounds of formula (IX) will preferably be dissolved in a solvent.

The reaction can be carried out at atmospheric pressure, reduced pressure or under elevated pressure, if appropriate under an inert gas, continuously or batchwise.

It might be advantageous to partly, almost completely or completely remove the HCl formed in the course of the reaction.

After completion or partial completion of the reaction, the reaction mixture can be worked up by the methods customary for the purpose by means of standard techniques. Examples thereof include filtration, aqueous work-up, and evaporation of solvents and/or other volatile compounds. These methods can also be combined with each other.

In general the solvent used is removed by customary methods, distillatively for example. The crude product can then be taken up in a non-water-miscible organic solvent, any impurities extracted with unacidified or acidified water, and the system can then be dried and the solvent removed under reduced pressure.

In case the reaction of the amino-benzoxazinones of formula (VIII) with compounds of formula (IX), is conducted in the absence of a base, preferably the solvent and optionally the excess of compounds of formula (IX) are removed by customary methods, e.g. by distillation.

Another option for work-up is to remove the HCl developed during the reaction in vacuo or by means of an inert gas flow, and then used the solution obtained without further purification in the subsequent reaction.

In case the reaction of the amino-benzoxazinones of formula (VIII) with compounds of formula (IX) is conducted in the presence of a base, after the ending of the reaction, preferably in a further step the reaction mixture is diluted by addition of water followed by phase separation. The solvent can then be removed by customary methods.

Generally the product is obtained with high purity. If necessary, for further purification it is possible to employ the typical methods such as crystallization, precipitation (for example by addition of an apolar solvent such as pentane, cyclohexane, heptane or toluene, or mixtures of said solvents) or chromatography.

The invention is illustrated by the following examples without being limited thereto or thereby.

EXAMPLES

The yields of the carbamates of formula (I), the carbamatbenzoxazinones of formula (VI), and the benzoxazinones of formula (VIII) were, unless stated otherwise, determined by means of quantitative HPLC:

Method A
Sample preparation:
  The samples of the products to be determined were weighed into a 100 ml standard flask which was made up to 100 ml with acetonitrile.
Chromatographic conditions:
  Column: Zorbax Eclipse XDB-C18 1.8 µm 50×4.6 mm from Agilent®
  Wavelength: 210 nm
  Eluent: gradient of A (0.1% by volume of $H_3PO_4$ in $H_2O$) and B (0.1% by volume of $H_3PO_4$ in acetonitrile); starting with 2% B, then B rising from 2% to 30% within 2 min, then B rising from 30% to 100% within 6 min, then 2 min 100% B, then back to 2% within 0.1 min.
  Flow rate: 1.4 ml/min
  Pressure: approx. 210 bar
Calibration:
  The calibration was effected with external standard. To establish the standard, a total of 5 samples of the pure substances were weighed in the following concentrations (precision+/−0.1 mg): approx. 0.02 g/l, approx. 0.04 g/l, approx. 0.06 g/l, approx. 0.08 g/l, approx. 0.10 g/l. With the aid of a suitable PC program, a calibration line was established. For the substances detailed above, this was a linear function. Standard deviation, correlation coefficient and straight-line equation were calculated. For each of the components, their concentration can thus be determined based on the particular external standard.

Method B
Sample preparation:
  The samples of the products to be determined were weighed into a 100 ml standard flask which was made up to 100 ml with acetonitril.
Chromatographic conditions:
  Column: Zorbax SB-Phenyl 1.8 µm 50×4.6 mm from Agilent®
  Wavelength: 210 nm
  Eluent: gradient of A (0.1% by volume of $H_3PO_4$ in $H_2O$) and B (acetonitrile); starting with 15% B, then B rising from 15% to 50% within 5 min, then B rising from 50% to 100% within 5 min, then 2 min 100% B, then back to 15% within 0.1 min.
  Flow rate: 1.3 ml/min
  Pressure: approx. 365 bar
Calibration:
  The calibration was effected with external standard. To establish the standard, a total of 5 samples of the pure substances were weighed in the following concentrations (precision+/−1-0.1 mg): approx. 0.01 WI, approx. 0.05 WI, approx. 0.10 WI, approx. 0.15 WI, approx. 0.20 WI. With the aid of a suitable PC program, a calibration line was established. For the substances detailed above, this was a linear function. Standard deviation, correlation coefficient and straight-line equation were calculated. For each of the components, their concentration can thus be determined based on the particular external standard.

1. Preparation of Carbamates of Formula (I)

Example 1.1

Methyl N-methyl-N-(methylcarbamothioyl)carbamate

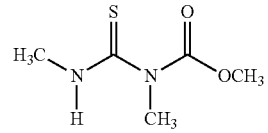

420.9 g (4.00 mol) N,N-dimethylthiourea with a purity of 99% were charged to 2000 g toluene. 507 g (4.78 mol) sodium carbonate was added and the suspension heated to 65° C. Afterwards 432.2 g (4.60 mol) methyl chloroformate were dosed in over 5 h at 65° C. The mixture was poststirred at the same temperature over 0.5 h. For work up, demineralized water was added under agitation and the phases separated. The aqueous phase was extracted with 800 g toluene and the organic phases were combined. The product content of the organic solution was determined with 15.15% by quant. HPLC (HPLC-method A; $t_R$=3.6 min), which corresponds to a chemical yield of 90.3%.

$^1$H-NMR (CDCl$_3$, 400 MHz): 10.1-10.3 (1H, s), 3.82 (3H, s), 3.66 (3H, s), 3.17 (3H, d).

Examples 1.2 and 1.3

Phenyl N-methyl-N-(methylcarbamothioyl)carbamate

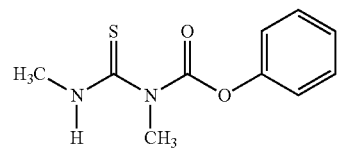

Example 1.2

N,N'-dimethyl thiourea of example 2.1 (0.66 mol) was dissolved in ethyl acetate. 106.0 g (1.00 mol) sodium carbonate were added and 156.6 g (1.00 mol) phenyl chloroformate were dosed over a period of 30 min with the temperature rising to 63° C. The mixture was poststirred at 66° C. for 0.5 h. Demineralized water was added under agitation at the same temperature and the phases separated. A vacuum was applied to the organic phase and 200 ml of a two-phase liquid were distilled off. The vessel was cooled to 5° C. and stirred for 1 h at this temperature. The product was collected by filtration and washed once with cyclohexane. The resulting solid was dried to yield 114.0 g (0.50 mol) of colourless crystals with a purity of 98% (HPLC-method B; $t_R$=5.93 min) and a melting point of 133-135° C. (corresponding chemical yield: 75%).

$^1$H-NMR (CDCl$_3$, 400 MHz): 10.5-10.6 (1H, s), 7.38-7.46 (2H, m), 7.24-7.32 (1H, m), 7.09-7.17 (2H, m), 3.89 (3H, s), 3.17 (3H, d).

Example 1.3

50.0 g (0.66 mol) methylisothiocyanate with a purity of 98% were added to ethyl acetate. 22.0 g (0.71 mol) of methyl amine were introduced at 20-30° C. with a dip tube. Nitrogen was bubbled through the solution for 14 h. 106.0 g (1.00 mol) sodium carbonate were added and 156.6 g (1.00 mol) phenyl chloroformate were dosed over a period of 30 min with the temperature rising from 30° C. to 60° C. The mixture was poststirred at 70° C. for 0.5 h. Demineralized water was added under agitation at the same temperature and the phases separated. A vacuum was applied to the organic phase and 100 ml of a two-phase liquid were distilled off. The vessel was cooled to 5° C. and stirred for 1 h at this temperature. The product was collected by filtration and washed once with 50 g of cyclohexane. The resulting solid was dried to yield 124.0 g (0.54 mol) of colourless crystals with a purity of 98% (HPLC-method B; $t_R$=5.93 min; corresponding chemical yield: 82.1%).

2. Preparation of Precursors and Intermediates for the Carbamates of Formula (I)

Example 2.1

N,N'-dimethyl thiourea

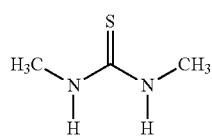

50.0 g (0.66 mol) methylisothiocyanate with a purity of 97% were added to xylene (isomeric mixture). 20.6 g (0.66 mol) of methyl amine were introduced at 20-30° C. with a dip tube resulting in the formation of two layers. The lower slightly yellow layer was separated, transferred to a rotary evaporator, and treated with a vacuum of 10 mbar at 50° C. for 30 min. Qualitative analytics (HPLC, GC) showed complete conversion to N,N'-dimethyl thiourea (no MITC detectable), the composition was 88% DMTU and 12% xylene (GC-area-%).

3. Preparation of carbamat-benzoxazinones of Formula (VI)

Examples 3.1 to 3.5

Phenyl N-(2,2,7-trifluoro-3-oxo-4-prop-2-ynyl-1,4-benzoxazin-6-yl)carbamate

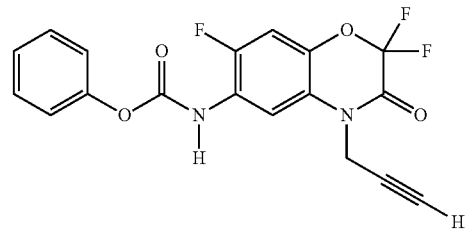 [SMILES: C#CCN1C(=O)C(F)(F)Oc2cc(F)c(NC(=O)Oc3ccccc3)cc21]

Example 3.1

182.9 g (0.700 mol) 6-Amino-2,2,7-trifluoro-4-prop-2-ynyl-4H-benzo[1,4]oxazin-3-one with a purity of 98.1% were dissolved in 521.1 g toluene and heated to reflux (110° C.) under agitation. 122.1 g (0.780 mol) phenyl chloroformate were added over 1 h at 107-112° C. (reflux) and the mixture afterwards poststirred over 1 h at the same temperature (HCl offgas). Low boilers were removed with a rotary evaporator under vacuum. 281.3 g (0.707 mol) of the product were obtained with 94.6% purity determined by quantitative HPLC method A ($t_R$=5.7 min; corresponding chemical yield 100%).

1H-NMR (500 MHz, CDCl$_3$): δ (ppm)=2.31 (t, 1H), 4.76 (d, 2H), 7.07 (d, 1H), 7.19-7.31 (m, 4H), 7.43 (t, 2H), 8.28 (d, 1H).

Example 3.2

53.2 g (0.200 mol) 6-Amino-2,2,7-trifluoro-4-prop-2-ynyl-4H-benzo[1,4]oxazin-3-one with a purity of 96.3% were dissolved in 500 mL acetonitrile. 18.48 g (0.22 mol) sodium bicarbonate were added. 34.4 g (0.22 mol) phenyl chloroformate were added slowly at 22° C. and the temperature was kept constant by an ice bath. The mixture was stirred for 3 h at room temperature. The solids were removed by filtration. 500 mL dichloromethane were added to the solution and the organic phase was washed three times with water. The organic phase was dried over MgSO$_4$ and evaporated to dryness. The residue was triturated with warm cyclohexane. The residue was removed by filtration and washed with cyclohexane. 74.0 g of the product were obtained as off-white solid, with a purity of 96.3% determined by quantitative HPLC method A ($t_R$=5.7 min), which corresponds to a chemical yield of 94.7%.

Example 3.3

1.5 g (5.8 mmol) 6-Amino-2,2,7-trifluoro-4-prop-2-ynyl-4H-benzo[1,4]oxazin-3-one with a purity of 98.4% were dissolved in 6 g THF. 0.95 g (6.1 mmol) phenyl chloroformate were added. A temperature rise from 23° C. to 32° C. was observed. The mixture was stirred for 1 h at room temperature. The mixture was evaporated to dryness. 2.2 g of the product with a purity of 96.2% determined by quantitative HPLC method A ($t_R$=5.7 min) were obtained, which corresponds to a chemical yield 97%.

Example 3.4

6.5 g (24.9 mmol) 6-Amino-2,2,7-trifluoro-4-prop-2-ynyl-4H-benzo[1,4]oxazin-3-one with a purity of 98.1% were dissolved in 18.8 g ethyl acetate. The solution was heated to 77° C. and 4.3 g (27.5 mmol) phenyl chloroformate were added within 30 min. The mixture was stirred for 1 h at 77° C. and evaporated to dryness. 9.95 g of the product with a purity of 94.6% determined by quantitative HPLC method A ($t_R$=5.7 min) were obtained, which corresponds to a chemical yield of 100%.

Example 3.5

In a nitrogen inerted, stirred reactor 119.8 g of dry ethyl acetate (100%) and 119.8 g (0.758 mol) of phenyl chloroformate (99%) was precharged and heated up to 85° C. (reflux conditions). 868.8 g (0.702 mol) of a 20.7% solution of 6-Amino-2,2,7-trifluoro-4-prop-2-ynyl-4H-benzo[1,4]oxazin-3-one in ethyl acetate was preheated to 60° C. and dosed over 2.5 h. During the dosage HCl gas was formed as co-product and sent to a scrubber operated with NaOH (10%). After a post reaction time of 0.5 h at 79° C. (reflux conditions), 634 g of the solvent was distilled off at normal pressure. Subsequently 698 g of fresh ethyl acetate (100%) was added and 647 g distilled off again. 876.9 g of dry DMF (100%) was added and 280.8 g of solvent (mainly ethyl acetate) was distilled off at 120-10 mbar and internal temperatures up to 50° C. 1112.0 g of a DMF solution containing 23.4% of the product determined by quantitative HPLC method B ($t_R$=6.9 min) was obtained, corresponding to 98.5% chemical yield.

4. Preparation of the Benzoxazinones of Formula (VII)

Examples 4.1 to 4.7

1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione

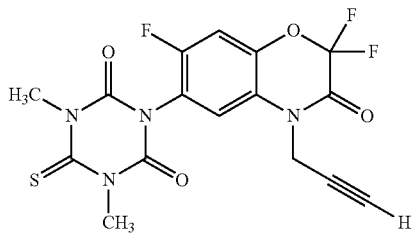

Example 4.1

4.49 g (20.0 mmol) phenyl N-methyl-N-(methylcarbamothioyl)carbamate and 7.84 g (20.0 mmol) phenyl N-[2,2,7-trifluoro-3-oxo-4-(prop-2-ynyl)-3,4-dihydro-2H-benzo[b][1,4]oxazin-6-yl]carbamate (purity 96%) were dissolved in 40 mL N,N-dimethylformamide (DMF), 0.33 g (4.0 mmol) sodium acetate were added and the mixture heated to 60° C. After 3.5 h 32 ml DMF were removed by distillation at 50° C. under reduced pressure. The product precipitated after addition of a mixture of 25 mL methanol and 25 mL H$_2$O. The solids were collected and washed with 10 mL water and 10 mL methanol. 7.8 g (purity by quant. HPLC 97.8 wt % corresponding to 93% chemical yield; HPLC-method A; $t_R$=5.9 min) of the title compound were obtained.

$^1$H-NMR (CDCl$_3$, 400 MHz): 7.27 (1H, d), 7.18 (1H, d), 4.76 (2H, s), 3.80 (6H, s), 2.38 (1H, s)

Example 4.2

0.56 g (2.5 mmol) phenyl N-methyl-N-(methylcarbamothioyl)carbamate and 0.98 g (2.5 mmol) phenyl N-[2,2,7-trifluoro-3-oxo-4-(prop-2-ynyl)-3,4-dihydro-2H-benzo[b][1,4]oxazin-6-yl]carbamate (purity 96%) were dissolved in 20 mL tetrahydrofuran (THF). 49 mg (0.50 mmol) potassium acetate were added and the mixture heated to 60° C. After 4 h the solvent was removed. The product solidified after addition of 10 g 60% aqueous methanol. The solids were collected and washed twice with 2 mL 60% aqueous methanol. 0.95 g (purity by quant. HPLC 99.5 wt % corresponding to 92% chemical yield; HPLC-method A; $t_R$=5.9 min) of the title compound were obtained.

Example 4.3

1.03 g (4.02 mmol) 6-amino-2,2,7-trifluoro-4-(prop-2-ynyl)-3,4-dihydro-2H-benzo[b][1,4]oxazin-3-one was dissolved in 20 mL THF. A solution of 0.63 g (4.02 mmol) phenyl chloroformate in THF was added at 55° C. The mixture was stirred for 30 min at this temperature. Formed HCl was stripped by a nitrogen stream. 8 mL DMF were added and THF distilled off under vacuum. 65 mg (0.79 mmol) sodium acetate and 0.97 g (4.02 mmol) phenyl N-methyl-N-(methylcarbamothioyl)carbamate (purity 93%) was added and the mixture stirred at 45° C. until HPLC showed complete conversion. 6 g DMF was removed by distillation under reduced pressure and the product precipitated after addition of 8 g 60% aqueous methanol. The solids were collected, washed twice with 60% aqueous methanol and dried in vacuum. 1.51 g (purity by quant. HPLC 97.3% corresponding to 97% chemical yield; HPLC-method A; $t_R$=5.9 min) of the title compound were obtained.

Example 4.4

3.24 g (20.0 mmol) methyl N-methyl-N-(methylcarbamothioyl)carbamate were dissolved in 30 g DMF and 0.21 g (2.0 mmol) Na$_2$CO$_3$ was added. The pressure was reduced to 12 mbar and the mixture heated to reflux (40-42° C.). 7.96 g (20.0 mmol) phenyl N-[2,2,7-trifluoro-3-oxo-4-(prop-2-ynyl)-3,4-dihydro-2H-benzo[b][1,4]oxazin-6-yl]carbamate (purity 94.5%) in 20 g DMF were added continuously over 60 min. Methanol formed in the course of the reaction was removed by co-distillation with DMF. The solvent volume was kept constant by addition of pure DMF from a second feed vessel. The mixture was stirred for another 30 min at this temperature and for 90 min at 25° C. The resulting solution (39.5 g) contained 20.2 wt % of the title compound corresponding to 96.5% chemical yield (HPLC-method A; $t_R$=5.9 min)

Example 4.5

In a nitrogen inerted, stirred reactor 118.7 g of dry ethyl acetate (100%) and 59.3 g (0.375 mol) of phenylchloroformate (99%) were precharged and heated up to 85° C. (reflux conditions). A solution of 100 g (0.354 mol) of 6-amino-2,2,7-trifluoro-4-(prop-2-ynyl)-3,4-dihydro-2H-benzo[b][1,4]oxazin-3-one (90.7%) in 400 g of ethyl acetate was preheated to 60° C. and dosed over 2.5 h. During the dosage HCl gas was formed as co-product and sent to a scrubber operated with NaOH (10%). After a post reaction time of 0.5 h at 79° C. (reflux conditions), 400 g of the solvent was distilled off at normal pressure. Subsequently 400 g of fresh ethyl acetate was added and distilled off again. 441.4 g of DMF was added and 162.8 g of solvent (mainly ethyl acetate) was distilled off at 120-10 mbar and internal temperatures up to 50° C. At 50° C. 80.1 g (0.350 mol) of phenyl N-methyl-N-(methylcarbamothioyl)carbamate (98.1%) was added followed by 5.8 g (0.071 mol) of dry sodium acetate (100%). The mixture was stirred 3.5 h at 50° C. Afterwards 258.0 g of DMF was distilled off at 5-10 mbar and internal temperatures up to 55° C. For precipitation of the title compound 601.8 g of a mixture methanol/water 3:2 was precharged in a second reactor and heated up to 50° C.

At 50° C. 1.8 g (0.0044 mol) of 1,5-dimethyl-6-thioxo-3-[2,2,7-trifluoro-3-oxo-4-(prop-2-ynyl)-3,4-dihydro-2H-benzo[b][1,4]oxazin-6-yl]-1,3,5-triazinane-2,4-dione was added. Then the concentrated DMF solution of the raw product was dosed in 1.5 h at 50° C. Afterwards the mixture was cooled down to 10° C. and stirred 0.5 h at 10° C. The precipitated product was isolated by filtration and washed twice with 150 g of a mixture methanol/water 3:2 precooled to 0° C. The wet filter cake was dried in a vacuum drying oven. 134.9 g (0.315 mol) of the title compound (96.3 wt % purity determined by quant. HPLC (HPLC-method B; $t_R$=7.1 min) were obtained (corresponding to 89% chemical yield).

Example 4.6

44 g (0.27 mol) methyl N-methyl-N-(methylcarbamothioyl)carbamate, purity 94.1%, in 414 g DMF were charged to a laboratory glass vessel. 4.64 g (44 mmol) $Na_2CO_3$ was added. The mixture was heated to reflux at 10 mbar/40° C. Afterwards 111 g (0.27 mol) phenyl N-[2,2,7-trifluoro-3-oxo-4-(prop-2-ynyl)-3,4-dihydro-2H-benzo[b][1,4]oxazin-6-yl]carbamate (purity 91.6%) in 372 g DMF was dosed in at 40° C. under reflux of DMF over 4 h (40° C., 10 mbar). The generated methanol was not condensed together with the DMF and so removed from the mixture. After poststirring of 30 min, the major part of DMF was distilled off (10-20 mbar, 50° C.). The vessel content was cooled to 20° C. and a mixture of 487 g MeOH and 487 g demineralized water was added for precipitation. The resulting suspension was cooled to 3° C. and the product was filtered, washed with water and dried in a vacuum cabinet at 50° C.

107 g (0.255 mol) of the product with a purity of 98.4% determined by quant. HPLC (HPLC-method A; $t_R$=5.9 min) have been obtained (corresponding to 94.5% chemical yield).

Example 4.7

0.38 g (2.0 mmol) ethyl N-methyl-N-(methylcarbamothioyl)carbamate with a purity of 91.9% was added to 3.5 g DMF. Under agitation, 0.76 g (2.0 mmol) phenyl N-[2,2,7-trifluoro-3-oxo-4-(prop-2-ynyl)-3,4-dihydro-2H-benzo[b][1,4]oxazin-6-yl]carbamate (98.5% purity) and 0.01 g (0.14 mmol) of NaOH powder were added at 35° C. After a post-stirring period of 2 h, a chemical yield 70.1% was determined by quantitative HPLC analytics (HPLC-method A; $t_R$=5.9 min) of the product solution.

Example 4.8

1,5-dimethyl-6-thioxo-3-(2,2,7-trifluoro-3-oxo-3,4-dihydro-2H-benzo[b][1,4]oxazin-6-yl]-1,3,5-triazinane-2,4-dione

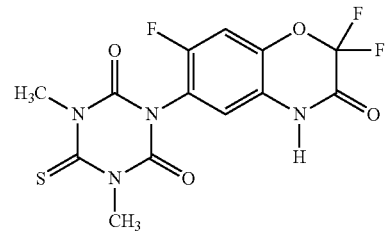 [SMILES: Cn1c(=S)n(C)c(=O)n(-c2cc3c(cc2F)OC(F)(F)C(=O)N3)c1=O]

0.97 g (5.0 mmol) methyl N-methyl-N-(methylcarbamothioyl)carbamate with a purity of 83.3% was dissolved in 4.2 g DMF. 0.14 g (1.7 mmol) sodium acetate was added. The mixture was stirred at 60° C. at a pressure of 25 mbar. Via syringe a solution of 1.32 g (3.7 mmol) phenyl N-(2,2,7-trifluoro-3-oxo-3,4-dihydro-2H-benzo[b][1,4]oxazin-6-yl)carbamate (purity 95.7%) in 4.2 g DMF was added within 2 h. From time to time fresh DMF was added to maintain the solvent volume. After a poststirring period of 1 h, a chemical yield 73% was determined by quantitative HPLC analytics (HPLC-method A; $t_R$=4.9 min) of the product solution.

$^1$H-NMR (DMSO-$d_6$, 400 MHz): 11.98 (1H, br), 10.07 (1H, br), 7.54 (1H, d), 7.40-7.49 (3H, m), 7.20-7.30 (3H, m).

The invention claimed is:
1. A compound of formula (I),

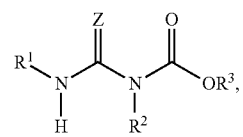

wherein
$R^1$ is H or $C_1$-$C_6$-alkyl;
$R^2$ is methyl;
$R^3$ is methyl, $C_1$-$C_6$-haloalkyl, $C_1$-$C_6$-cyanoalkyl, $C_1$-$C_6$-nitroalkyl, aryl, 5-or 6-membered heteroaryl or aryl-$C_1$-$C_6$-alkyl,
wherein the aryl or heteroaryl rings are unsubstituted, partially or fully halogenated, or substituted by one to five substituents selected from the group consisting of CN, $NO_2$, $C_1$-$C_6$-alkyl $C_1$-$C_6$-haloalkyl, OH, $C_1$-$C_6$-alkoxy, $C_1$-$C_6$-haloalkoxy, formyl, $C_1$-$C_6$-alkylcarbonyl, hydroxycarbonyl, and $C_1$-$C_6$-alkoxycarbonyl;
and
Z is S.
2. The compound of claim 1, wherein $R^3$ is methyl or aryl, wherein the aryl ring is unsubstituted or substituted by one halogen atom or one $C_1$-$C_6$-alkyl group.
3. The compound of claim 1, wherein $R^1$ is methyl.
4. The compound of claim 1, wherein $R^1$ and $R^3$ are both methyl.

5. The compound of claim 1, wherein $R^1$ is methyl and $R^3$ is phenyl.

6. A process for the preparation of the compound of formula (I) as claimed in claim 1 wherein a compound of formula (II),

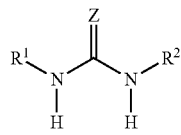 (II)

is reacted with the compound of formula (III)

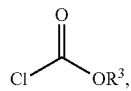 (III)

in the presence of a base.

7. A process for preparing a compound of formula (II) comprising a) reacting a compound of formula (IV)

 (IV)

wherein $R^1$ is H or $C_1$-$C_6$-alkyl; and

Z is S

With a compound of formula (V)

 (V)

wherein $R^2$ is methyl.

8. The process as claimed in claim 7, wherein the compound of formula (II) is not isolated, and the reaction mixture obtained in step a) is directly used in the reaction to give carbamates of formula (I).

* * * * *